(12) United States Patent
Welch et al.

(10) Patent No.: US 9,174,934 B2
(45) Date of Patent: Nov. 3, 2015

(54) ARYL TETRAFLUOROSULFANYL COMPOUNDS

(71) Applicant: THE RESEARCH FOUNDATION FOR THE STATE UNIVERSITY OF NEW YORK, Albany, NY (US)

(72) Inventors: John Welch, Albany, NY (US); Linbin Zhong, Albany, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 14/436,474

(22) PCT Filed: Mar. 12, 2013

(86) PCT No.: PCT/US2013/030329
§ 371 (c)(1),
(2) Date: Apr. 16, 2015

(87) PCT Pub. No.: WO2014/062221
PCT Pub. Date: Apr. 24, 2014

(65) Prior Publication Data
US 2015/0246877 A1    Sep. 3, 2015

Related U.S. Application Data

(60) Provisional application No. 61/715,482, filed on Oct. 18, 2012.

(51) Int. Cl.
*C07C 323/07* (2006.01)
*C07C 323/09* (2006.01)
*C07C 323/63* (2006.01)
*C07C 319/14* (2006.01)
*C09K 19/04* (2006.01)

(52) U.S. Cl.
CPC ............ *C07C 323/07* (2013.01); *C07C 319/14* (2013.01); *C07C 323/09* (2013.01); *C07C 323/63* (2013.01); *C09K 19/04* (2013.01)

(58) Field of Classification Search
None
See application file for complete search history.

(56) References Cited

U.S. PATENT DOCUMENTS

| 7,592,491 | B2 | 9/2009 | Umemoto |
| 7,820,864 | B2 | 10/2010 | Umemoto |
| 7,851,646 | B2 | 12/2010 | Umemoto |

FOREIGN PATENT DOCUMENTS

| DE | 10008505 A1 | 10/2000 |
| WO | 2008/118787 A1 | 10/2008 |
| WO | 2009/114409 A2 | 9/2009 |
| WO | 2010/022001 A1 | 2/2010 |
| WO | 2010/033930 A1 | 3/2010 |

OTHER PUBLICATIONS

International Search Report for International Application No. PCT/US2013/030329, dated Jul. 3, 2013.
Ou, Xiaobo et al., "Oxidative fluorination of S, Se and Te compounds", Journal of Fluorine Chemistry, 2000, vol. 101, No. 2, pp. 279-283.
Kirsch, P. et al., "Bis(4-nitrophenyl)tetrafluorosulfuranes: Synthesis, Isomerization and Structural Characterization", Journal of American Chemical Society, 1999, vol. 121, No. 49, pp. 11277-11280.
Denny, D.B. et al., "Dialkyl- and Diaryltetrafluoropersulfuranes", Journal of American Chemical Society, 1973, vol. 95, No. 24, pp. 8191-8192.
Kirsch, Peer, et al. "Liquid Crystals Based on Hypervalent Sulfur Fluorides: Pentafluorosulfuranyl as Polar Terminal Group"; Angewandte Chemie International Edition; 1999; pp. 1989-1992; vol. 38; WILEY-VCH Verlag GmbH, Weinheim.
Kirsch, Peer, et al. "Nematic Liquid Crystals for Active Matrix Displays: Molecular Design and Synthesis"; Angewandte Chemie International Edition; 2000; pp. 4216-4235; vol. 39; WILEY-VCH Verlag GmbH, Weinheim.
Kirsch, P.; Binder, W.; Hahn, A.; Jahrling, K.; Lenges, M.; Lietzau, L.; Maillard, D.; Meyer, V.; Poetsch, E.; Ruhl, A.; Unger, G.; Frolich, R. Super-fluorinated liquid crystals: towards the limits of polarity. Eur. J. Org. Chem. 2008, 3479-3487.
Kirsch, P.; Hahn, A. Liquid crystals based on hypervalent sulfur fluorides: Exploring the steric effects of ortho-fluorine substituents. Eur. J. Org. Chem. 2005, 3095-3100.
Matsushita, T.; Koseki, S. Theoretical Study on Mesogenic Core Structures of Nematic Liquid Crystalline Compounds. J. Phys. Chem. B 2005, 109, 13493-98.
Kirsch, Peer, et al. "Liquid Crystals Based on Hypervalent Sulfur Fluorides: The trans- (Trifluoromethyl) tetrafluorosulfuranyl Group"; European Journal of Organic Chemistry; 2006; pp. 1125-1131; WILEY-VCH Verlag GmbH & Co. KGaA, Weinheim.
Umemoto, Teruo, et al. "Discovery of practical production processes for arylsulfur pentafluorides and their higher homologues, bis- and tris(sulfur pentafluorides): Beginning of a new era of "super-trifluoromethyl" arene chemistry and its industry"; Beilstein Journal of Organic Chemistry; 2012, pp. 461-471; vol. 8.
Darragh, John I., et al. "Trans-Chlorotetrafluoro(trifluoromethyl)sulphur and its Reactions with Olefins and Acetylenes"; Journal of the Chemical Society, Dalton Transactions; 1973; pp. 2289-2293.

(Continued)

*Primary Examiner* — Brian J Davis
(74) *Attorney, Agent, or Firm* — Heslin Rothenberg Farley & Mesiti P.C.

(57) ABSTRACT

The invention provides compounds of the Formula (I), methods of making the compounds, and devices comprising the compounds.

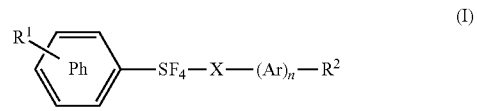

20 Claims, 3 Drawing Sheets

(56) References Cited

OTHER PUBLICATIONS

Abe, Takashi, et al. "CIS and Trans Isomers of BIS(Perfluoroalkyl)Sulfur Tetrafluorides"; Inorganic and Nuclear Chemistry Letters; 1973; pp. 465-468; vol. 9, No. 4; Pergamon Press; Great Britain.

Gupta, Krishna D., et al. "Syntheses of CF3SF4-Substituted Compounds"; Inorganic Chemistry; 1985; pp. 1457-1460; vol. 24; No. 10; American Chemical Society.

Kitazume, Tomoya, et al. Some Chemistry of Fluorinated Octahedral Sulfur Compounds; Journal of the American Chemical Society; Jan. 18, 1978; pp. 492-496; vol. 100; Issue 2.

Kirsch, Peer, et al. "Liquid crystals based on hypervalent sulfur fluorides Part 4. [1] Pentafluorosulfanyl alkanes and olefins"; 2006; pp. 610-619; vol. 127; Elsevier B.V., Journal of Fluorine Chemistry.

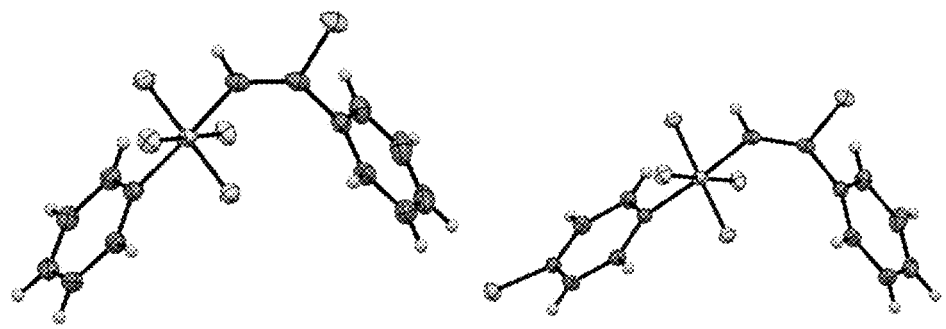
FIG. 1 - Example 1a                    FIG. 2 - Example 1b
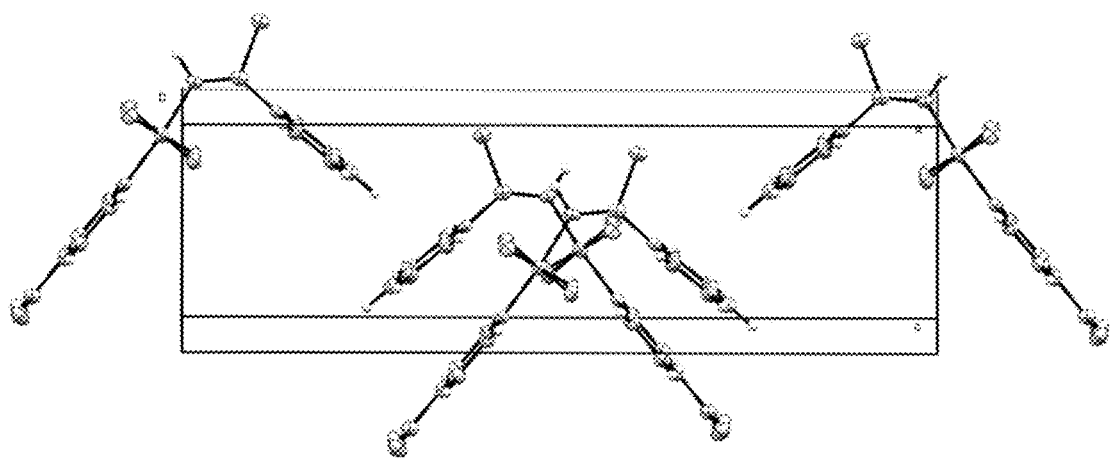
FIG. 3 - Example 1c in a polar space group

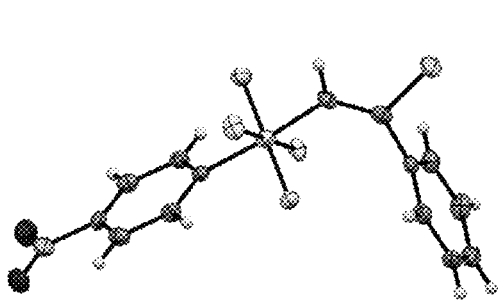
FIG. 4 - Example 1c
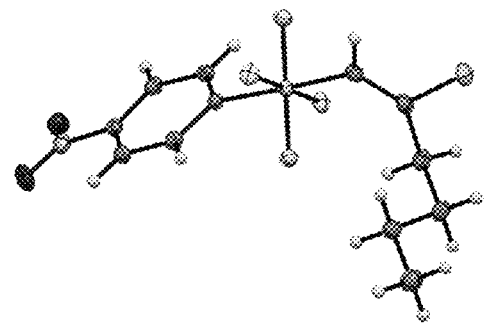
FIG. 5 - Example 1d
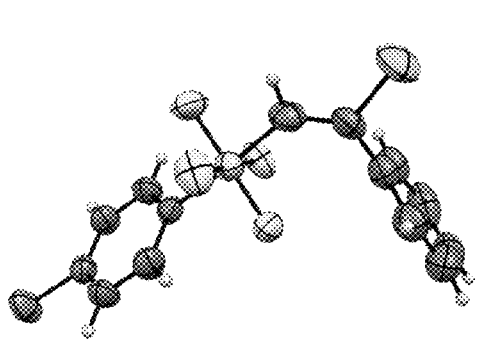
FIG. 6 - Example 1e
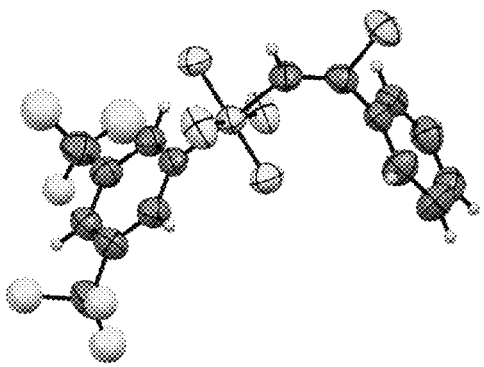
FIG. 7 - Example 1g
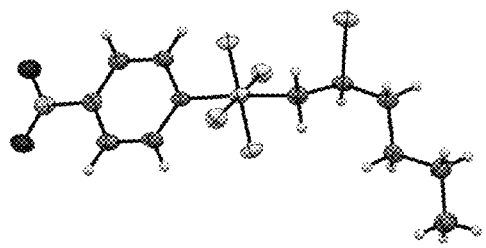
FIG. 8 - Example 2
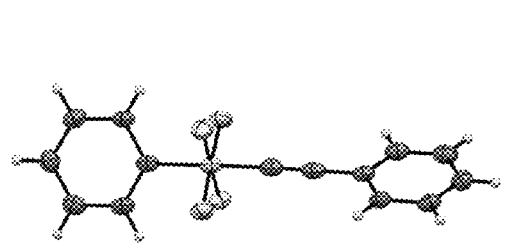
FIG. 9 - Example 6a

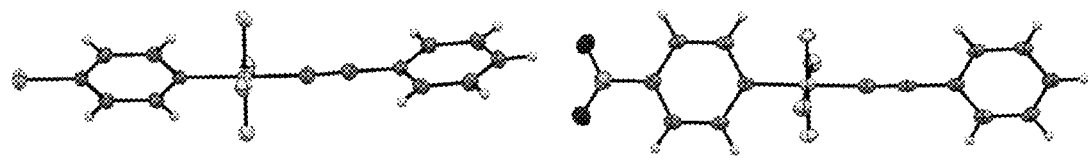
FIG. 10 - Example 6b        FIG. 11 - Example 6c
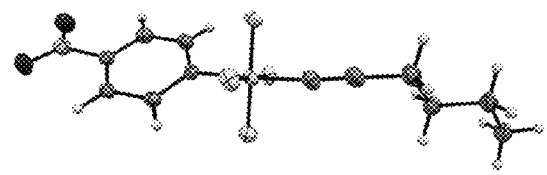
FIG. 12 - Example 6d
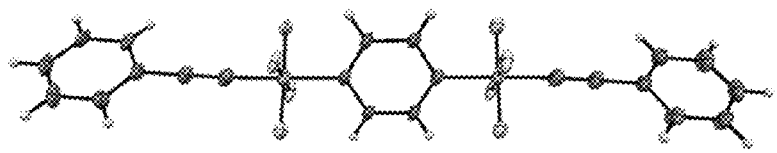
FIG. 13 - Example 6e
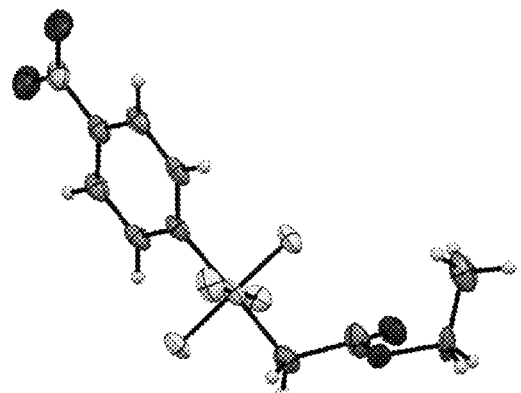
FIG. 14 - Example 8

ARYL TETRAFLUOROSULFANYL COMPOUNDS

CROSS-REFERENCE TO RELATED APPLICATIONS

This application is a U.S. National Phase filing under section 371 of International Application No. PCT/US2013/030329 filed on Mar. 12, 2013 and published in English on Apr. 24, 2014 as WO 2014/062221 and claims priority to U.S. Provisional Application No. 61/715,482, filed Oct. 18, 2012. The entire disclosures of each of the prior applications are herein incorporated by reference in their entirety.

GOVERNMENT RIGHTS STATEMENT

This invention was made with U.S. Government support under CHE0957544 awarded by National Science Foundation. The U.S. Government has certain rights in the invention.

FIELD OF THE INVENTION

The present invention generally relates to aryl tetrafluorosulfanyl compounds, to processes for the preparation of the compounds, and to devices comprising the compounds.

BACKGROUND OF THE INVENTION

There is strong interest in methods for the preparation of selectively fluorinated organic compounds, due in part to the profound influence that fluorine incorporation can have on the physical and chemical properties and biological activity of molecules.

Hypervalent sulfur fluorides possess an octahedral geometry unlike carbon-based fluoroorganic systems, which allows the design of linear trans-tetrafluorosulfanyl bridged structures which are of particular interest for highly fluorinated materials, such as liquid crystal for active matrix LCDs (Kirsch, P., et al., *Bis(4-nitrophenyl)tetrafluorosulfuranes: Synthesis, Isomerization and Structural Characterization*. Journal of the American Chemical Society, 1999. 121(49): p. 11277-11280).

While hypervalent sulfur fluorides, e.g., tetrafluorosulfanyl ($SF_4$) compounds, are known to be useful in various applications, such as in electro-optical display devices, these compounds have traditionally been prepared by direct fluorination, which has several significant limitations. For example, the substrates suitable for the oxidative fluorination step must themselves be unreactive toward fluorination. In other words, the substrates are generally limited to electron withdrawing group-substituted diaryl sulfides or trifluoromethylthioarenes. This requirement inherently restricts the nature and type of substitution that can be employed with the $SF_4$ group.

Thus, a need exists for improved methods of preparing tetrafluorosulfanyl compounds that are not limited by the requirement for direct fluorination, and for tetrafluorosulfanyl compounds that can accommodate a broader variety and nature of substitution.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Briefly, the present invention satisfies the need for, inter alia, new aryl tetrafluorosulfanyl compounds, improved processes for the preparation of aryl tetrafluorosulfanyl compounds, and for devices comprising the compounds. The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

Certain embodiments of the presently-disclosed compounds, devices, and processes have several features, no single one of which is solely responsible for their desirable attributes. Without limiting the scope of these compounds, devices, and processes as defined by the claims that follow, their more prominent features will now be discussed briefly. After considering this discussion, and particularly after reading the section of this specification entitled "Detailed Description of the Invention," one will understand how the features of the various embodiments disclosed herein provide a number of advantages over the current state of the art. These advantages may include, without limitation, improved methods of preparing tetrafluorosulfanyl compounds, provision of new tetrafluorosulfanyl compounds, and devices incorporating the compounds.

In one aspect, the invention relates to compounds of the Formula (I)

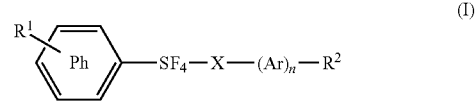

wherein
X and X' are independently selected from

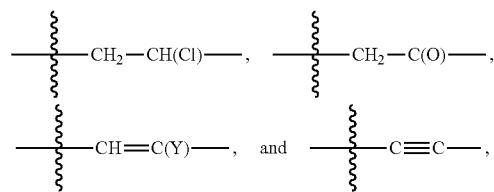

wherein

represents the point of connection (i.e., a bond) to $SF_4$ residue.

Y is selected from hydrogen and chlorine.

Ar and Ar' are independently selected from aryl and heteroaryl, each optionally substituted by one or more substituents in addition to $R^2$ or $R^{2'}$ independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$.

n and n' are independently 0 or 1.

Ph ring is a phenyl ring optionally substituted by up to four substituents in addition to $R^1$, independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$.

$R^1$, $R^2$, and $R^{2'}$ are independently absent or selected from hydrogen, halogen, hydroxy, trifluoromethyl, pentafluorosulfanyl, cyano, nitro, carboxy, amino, mono- or di-$C_{1-4}$ hydrocarbylamino, carbocyclic and heterocyclic groups having from 3 to 12 ring members; and a group A-B wherein A is a bond, O, CO, $Z^1C(Z^2)$, $C(Z^2)Z^1$, $Z^1C(Z^2)Z^1$, S, SO, $SO_2$, $NR^c$, $SO_2NR^c$ or $NR^cSO_2$, and B is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, and carbocyclic and heterocyclic groups having from 3 to 12 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy, and wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$; and $R^1$ may additionally be —$SF_4$—X'—$(Ar')_{n'}$—$R^{2'}$; with the provisos that (a) when X is

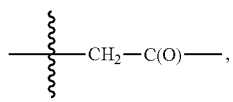

n is 0 and $R^2$ is A-B, where A is O; and (b) when X' is

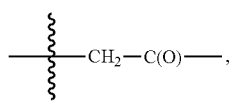

n' is 0 and $R^{2'}$ is A-B, where A is O.

$R^c$ is selected from hydrogen and $C_{1-4}$ hydrocarbyl.

$Z^1$ and $Z^2$ are independently selected from O, S, and NR.

In another aspect, the invention relates to a device, for example, an electro-optical display device (e.g., a liquid crystal display (LCD)), which includes a compound of Formula (I).

In another aspect, the invention relates to a process for preparing compounds of Formula (I), which includes the reaction of an aryl chlorotetrafluorosulfane compound of the formula:

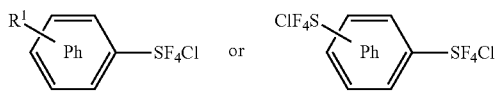

with an alkene or alkyne compound of the formula:

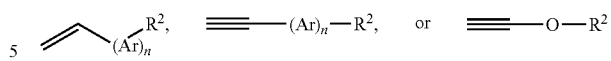

wherein each of Ph, Ar, n, $R^1$, and $R^2$ are as defined above, and optionally thereafter converting one compound of the Formula (I) into another compound of the Formula (I).

These and other features and advantages of this invention will become apparent from the following detailed description of the various aspects of the invention taken in conjunction with the appended claims and the accompanying drawings.

BRIEF DESCRIPTION OF THE DRAWINGS

FIG. 1 shows the structure of Example 1a as determined by single crystal X-ray diffraction.

FIG. 2 shows the structure of Example 1b as determined by single crystal X-ray diffraction.

FIG. 3 shows the structure of Example 1c in a polar space as determined by single crystal X-ray diffraction.

FIG. 4 shows the structure of Example 1c as determined by single crystal X-ray diffraction.

FIG. 5 shows the structure of Example 1d as determined by single crystal X-ray diffraction.

FIG. 6 shows the structure of Example 1e as determined by single crystal X-ray diffraction.

FIG. 7 shows the structure of Example 1g as determined by single crystal X-ray diffraction.

FIG. 8 shows the structure of Example 2 as determined by single crystal X-ray diffraction.

FIG. 9 shows the structure of Example 6a as determined by single crystal X-ray diffraction.

FIG. 10 shows the structure of Example 6b as determined by single crystal X-ray diffraction.

FIG. 11 shows the structure of Example 6c as determined by single crystal X-ray diffraction.

FIG. 12 shows the structure of Example 6d as determined by single crystal X-ray diffraction.

FIG. 13 shows the structure of Example 6e as determined by single crystal X-ray diffraction.

FIG. 14 shows the structure of Example 8 as determined by single crystal X-ray diffraction.

DETAILED DESCRIPTION OF THE INVENTION

The present invention is generally directed to aryl tetrafluorosulfanyl compounds, to processes for the preparation of the compounds, and to devices comprising the compounds.

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, which are herein incorporated by reference in their entirety.

The term "hydrocarbyl" is a generic term encompassing $C_1$-$C_{10}$ aliphatic, alicyclic and aromatic groups having an all-carbon backbone, except where otherwise stated. Examples of hydrocarbyl groups include alkyl, cycloalkyl, alkenyl, cycloalkenyl, alkynyl, aryl, cycloalkylalkyl, cycloalkenylalkyl, and carbocyclic aralkyl, aralkenyl and aralkynyl groups. Within the sub-set of hydrocarbyl groups are those having 1 to 8 carbon atoms, examples including $C_{1-6}$ hydrocarbyl groups, such as $C_{1-4}$ hydrocarbyl groups (e.g., $C_{1-3}$ hydrocarbyl groups or $C_{1-2}$ hydrocarbyl groups). Specific examples of hydrocarbyl groups include any individual value or combination of values selected from $C_1$, $C_2$, $C_3$, $C_4$, $C_5$, $C_6$, $C_7$, $C_8$, $C_9$, and $C_{10}$, hydrocarbyl groups. Hydrocarbyl includes any substituent comprised of hydrogen and carbon as the only elemental constituents.

The term "alkyl" covers both straight chain and branched hydrocarbon structures and combinations thereof. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Within the sub-set of alkyl groups are those having 1 to 8 carbon atoms, particular examples being $C_{1-6}$ alkyl groups, such as $C_{1-4}$ alkyl groups (e.g. $C_{1-3}$ alkyl groups or $C_{1-2}$ alkyl groups).

Examples of cycloalkyl groups are those derived from cyclopropane, cyclobutane, cyclopentane, cyclohexane and cycloheptane. Within the sub-set of cycloalkyl groups are cycloalkyl groups having from 3 to 8 carbon atoms, particular examples being $C_{3-6}$ cycloalkyl groups. Cycloalkyl, if not otherwise limited, refers to monocycles, bicycles and polycycles.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups are those having 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups are those having from 3 to 8 carbon atoms, for example, $C_{3-6}$ cycloalkenyl groups.

Examples of alkynyl groups include, but are not limited to, ethynyl and 2-propynyl (propargyl) groups. Within the sub-set of alkynyl groups are those having 2 to 8 carbon atoms, particular examples being $C_{2-6}$ alkynyl groups, such as $C_{2-4}$ alkynyl groups.

Examples of aryl groups, which are defined below, include substituted and unsubstituted phenyl and naphthyl groups.

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems. In general, such groups may be monocyclic for bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members.

As used herein, the term "optionally substituted" may be used interchangeably with "unsubstituted or substituted". The term "substituted" refers to the replacement of one or more hydrogen atoms in a specified group with a specified radical. Unless otherwise specified, a "substituted" residue (e.g., a hydrocarbyl, alkyl, aryl, heteroaryl, cycloalkyl, heterocyclyl, hydrocarbyloxy, etc.) refers to a residue wherein one or more hydrogen atoms in each residue are independently replaced with halogen, haloalkyl, alkyl, acyl, alkoxyalkyl, hydroxyloweralkyl, phenyl, heteroaryl, benzenesulfonyl, hydroxy, hydrocarbyloxy, haloalkoxy, carboxy, alkoxycarbonyl [—C(=O)O-alkyl], alkoxycarbonylamino [—HNC(=O)O-alkyl], carboxamido [—C(=O)NH$_2$], alkylaminocarbonyl [—C(=O)NH-alkyl], cyano, carbonyl, acetoxy, nitro, amino, alkylamino, dialkylamino, mercapto, alkylthio, sulfoxide, sulfone, sulfonylamino, acylamino, amidino, aryl, benzyl, heterocyclyl, phenoxy, benzyloxy, heteroaryloxy, hydroxyimino, alkoxyimino, oxaalkyl, aminosulfonyl, trityl, amidino, guanidino, ureido, or benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The term "hydrocarbyloxy" refers to a hydrocarbyl group attached to the parent structure through an oxygen. Examples of hydrocarbyloxy groups include saturated hydrocarbyloxy such as alkoxy (e.g. $C_{1-6}$ alkoxy, more usually $C_{1-4}$ alkoxy such as ethoxy and methoxy, particularly methoxy), cycloalkoxy (e.g. $C_{3-6}$ cycloalkoxy such as cyclopropyloxy, cyclobutyloxy, cyclopentyloxy and cyclohexyloxy) and cycloalkylalkoxy (e.g. $C_{3-6}$ cycloalkyl-$C_{1-2}$ alkoxy such as cyclopropylmethoxy). For the purpose of this application, alkoxy includes methylenedioxy and ethylenedioxy.

The term "oxaalkyl" refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see Naming and Indexing of Chemical Substances for Chemical Abstracts, published by the American Chemical Society, 196, but without the restriction of 127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Unless otherwise specified, "acyl" refers to formyl and to groups of 1, 2, 3, 4, 5, 6, 7, 8, 9, and 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. A subset of acyl is $C_1$-$C_4$ acyl. The double bonded oxygen, when referred to as a substituent itself is called "oxo".

"Acyloxy" refers to an acyl group attached to a parent structure through an oxygen.

Unless otherwise specified, "aryl" and "heteroaryl" mean (i) a phenyl group (or benzene) or a monocyclic 5- or 6-membered heteroaromatic ring containing 1-4 heteroatoms independently selected from O, N, and S; (ii) a bicyclic 9- or 10-membered aromatic or heteroaromatic ring system containing 0-4 heteroatoms independently selected from O, N, and S; or (iii) a tricyclic 13- or 14-membered aromatic or heteroaromatic ring system containing 0-5 heteroatoms independently selected from O, N, and S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloalkyl residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

Substituents (e.g. R″) are generally defined when introduced and retain that definition throughout the specification and in all independent claims.

Although this invention is susceptible to embodiment in many different forms, certain embodiments of the invention are shown and described. It should be understood, however, that the present disclosure is to be considered as an exemplification of the principles of this invention and is not intended to limit the invention to the embodiments illustrated.

As used herein, and as would be understood by the person of skill in the art, the recitation of "a compound"—unless expressly further limited—is intended to include salts of that compound. Thus, for example, the recitation "a compound of the Formula (I)" as depicted above, in which $R^1$ is COOH, would include salts in which $R^1$ is COO$^-$M$^+$, wherein M is any counterion. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools.

In one aspect, the invention provides compounds of the Formula (I):

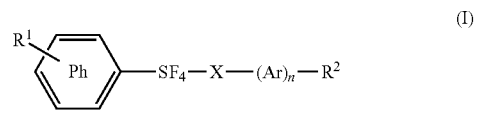

wherein:
X and X' are independently selected from

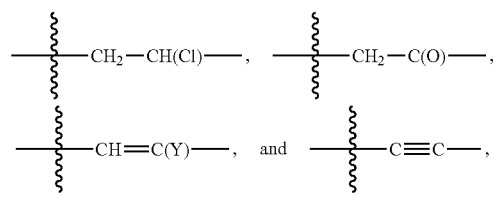

wherein

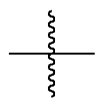

represents the point of connection to SF$_4$ residue;
Y is selected from hydrogen and chlorine;
Ar and Ar' are independently selected from aryl and heteroaryl, each optionally substituted by one or more substituents in addition to $R^2$ or $R^{2'}$. The one or more optional substituents are independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or SO$_2$;
n and n' are independently 0 or 1. When n is 0, Ar is not present, and when n' is 0, Ar' is not present.

Ph ring is a phenyl ring optionally substituted by up to four substituents (i.e., 0, 1, 2, 3, or 4 substituents) in addition to $R^1$. The up to four substituents in addition to $R^1$ are independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$;

$R^1$, $R^2$, and $R^{2'}$ are independently absent or selected from hydrogen, halogen, hydroxy, trifluoromethyl, pentafluorosulfanyl, cyano, nitro, carboxy, amino, mono- or di-$C_{1-4}$ hydrocarbylamino, carbocyclic and heterocyclic groups having from 3 to 12 ring members; and a group A-B wherein A is a bond, O, CO, $Z^1C(Z^2)$, $C(Z^2)Z^1$, $Z^1C(Z^2)Z^1$, S, SO, $SO_2$, $NR^c$, $SO_2NR^c$ or $NR^cSO_2$, and B is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, and carbocyclic and heterocyclic groups having from 3 to 12 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy, and wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$; and $R^1$ may additionally be —$SF_4$—X'—$(Ar')_{n'}$—$R^{2'}$; with the provisos that (a) when X is

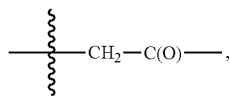

n is 0 and $R^2$ is A-B, where A is O; and (b) when X' is

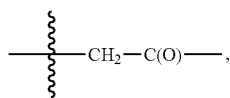

n' is 0 and $R^{2'}$ is A-B, where A is O;

$R^c$ is selected from hydrogen and $C_{1-4}$ hydrocarbyl; and $Z^1$ and $Z^2$ are independently selected from O, S, and $NR^c$.

In some embodiments, the compound of Formula (I) is a compound of Formula (I-i) to (I-iv):

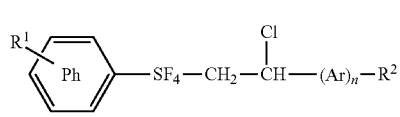
(I-i)

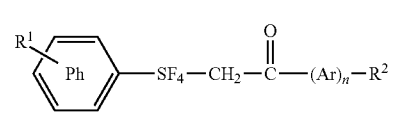
(I-ii)

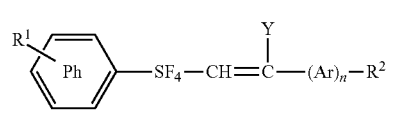
(I-iii)

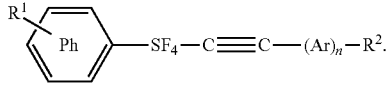
(I-iv)

In various embodiments, $R^1$ may be positioned ortho, meta, or para to the $SF^4$ residue on Ph, as shown below.

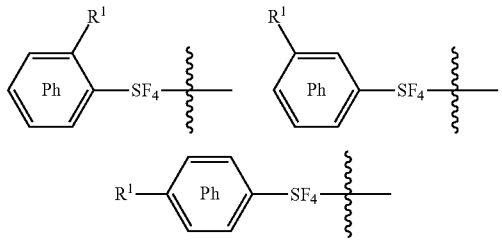

In some embodiments, the up to four substituents in addition to $R^1$ on the Ph ring are different. In some embodiments, the up to four substituents in addition to $R^1$ on the Ph ring are the same.

In certain embodiments, Ph is pentafluorobenzene. In some embodiments, Ph ring is a phenyl ring substituted only by $R^1$. In some embodiments, the Ph ring is a phenyl ring substituted by $R^1$ and one or more additional substituents independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$.

In some embodiments, $R^1$ is —$SF_4$—X'—$(Ar')_{n'}$—$R^{2'}$.

$R^1$, $R^2$, and, when present, $R^{2'}$, are independently absent or selected from hydrogen, halogen, hydroxy, trifluoromethyl, pentafluorosulfanyl, cyano, nitro, carboxy, amino, mono- or di-$C_{1-4}$ hydrocarbylamino, carbocyclic and heterocyclic groups having from 3 to 12 ring members; and a group A-B wherein A is a bond, O, CO, $Z^1C(Z^2)$, $C(Z^2)Z^1$, $Z^1C(Z^2)Z^1$, S, SO, $SO_2$, $NR^c$, $SO_2NR^c$ or $NR^cSO_2$, and B is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, and carbocyclic and heterocyclic groups having from 3 to 12 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy, and wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$; and $R^1$ may additionally be —$SF_4$—X'—$(Ar')_{n'}$—$R^{2'}$; with the provisos that (a) when X is

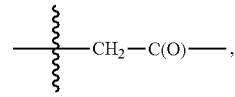

n is 0 and $R^2$ is A-B, where A is O; and (b) when X' is

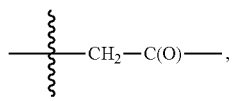

n' is 0 and $R^{2'}$ is A-B, where A is O;

In some embodiments, $R^1$, $R^2$, and $R^{2'}$ are independently absent or selected from hydrogen, fluorine, chlorine, bromine, trifluoromethyl, pentafluorosulfanyl, cyano, nitro, carboxy, amino, mono- or di-$C_{1-4}$ hydrocarbylamino; and a group A-B wherein A is a bond, O, CO, C(=O)O, OC(=O), OC(=O)O, or $NR^c$; and $R^1$ may additionally be —$SF_4$—X'—(Ar')$_{n'}$—$R^{2'}$.

In some embodiments, $R^1$, $R^2$, and $R^{2'}$ are independently absent, or independently represent a group A-B; and $R^1$ may additionally be —$SF_4$—X'—(Ar')$_{n'}$—$R^{2'}$. In some embodiments, B is hydrogen or a $C_{1-8}$ hydrocarbyl group optionally substituted by one or more substituents selected from hydroxy, oxo, halogen, cyano, nitro, carboxy, amino, and carbocyclic and heterocyclic groups having from 3 to 6 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy, where one or more carbon atoms of the $C_{1-8}$ hydrocarbyl group may optionally be replaced by O, CO, S, SO, $SO_2$, $NR^c$, OC(=O), C(=O)O or OC(=O)O.

In some embodiments, $R^1$, $R^2$, and $R^{2'}$ are independently absent, or independently represent a group A-B where A is O; and $R^1$ may additionally be —$SF_4$—X'—(Ar')$_{n'}$—$R^{2'}$.

In certain embodiments, $R^1$, $R^2$, and $R^{2'}$ are independently absent or selected from hydrogen, fluorine, chlorine, bromine, trifluoromethyl, cyano, nitro, carboxy, amino; and a group A-B wherein A is a bond, O, CO, C(=O)O, OC(=O), OC(=O)O, or $NR^c$ and B is hydrogen, a carbocyclic or heterocyclic group having from 3 to 6 ring members, or a $C_{1-8}$ hydrocarbyl group optionally substituted by one or more substituents selected from hydroxy, oxo, halogen, cyano, nitro, amino, or mono- or di-$C_{1-4}$ hydrocarbylamino, and wherein one or more carbon atoms of the $C_{1-8}$ hydrocarbyl group may optionally be replaced by O, CO, S, SO, $SO_2$, $NR^c$, OC(=O), C(=O)O or OC(=O)O; and $R^1$ may additionally be —$SF_4$—X'—(Ar')$_{n'}$—$R^{2'}$.

In some embodiments, $R^1$, $R^2$, and $R^{2'}$ are independently absent or selected from hydrogen, halogen, nitro, and a $C_{1-8}$ hydrocarbyl group wherein one or more carbon atoms of the $C_{1-8}$ hydrocarbyl group may optionally be replaced by O, CO, S, SO, $SO_2$, $NR^c$, OC(=O), C(=O)O or OC(=O)O; and $R^1$ may additionally be —$SF_4$—X'—(Ar')$_{n'}$—$R^{2'}$.

In certain embodiments, $R^1$, $R^2$, and $R^{2'}$ are independently selected from hydrogen, halogen, nitro, and an optionally substituted $C_{1-8}$ hydrocarbyl group wherein one or more carbon atoms of the $C_{1-8}$ hydrocarbyl group may optionally be replaced by O, CO, S, SO, $SO_2$, $NR^c$, OC(=O), C(=O)O or OC(=O)O; and wherein $R^1$ may additionally be —$SF_4$—X'—(Ar')$_{n'}$—$R^{2'}$.

In certain embodiments, $R^1$, $R^2$, and $R^{2'}$ are independently absent or selected from hydrogen, halogen, nitro, and an unsubstituted $C_{1-8}$ hydrocarbyl group, wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$; and $R^1$ may additionally be —$SF_4$—X'—(Ar')$_{n'}$—$R^{2'}$.

In some embodiments, one of $R^1$ and $R^2$ is $Z^a$, and the other is $Z^b$, wherein $Z^a$ is selected from nitro, cyano, carboxy, and trifluoromethyl; and $Z^b$ is selected from hydroxy, $C_{1-8}$ hydrocarbyloxy, and mono- or di-$C_{1-4}$ hydrocarbylamino.

In some embodiments, $R^1$ is —$SF_4$—X'—(Ar')$_{n'}$—$R^{2'}$, and one of $R^2$ and $R^{2'}$ is $Z^a$, and the other is $Z^b$, wherein $Z^a$ is selected from nitro, cyano, carboxy, and trifluoromethyl; and $Z^b$ is selected from hydroxy, $C_{1-8}$ hydrocarbyloxy, and mono- or di-$C_{1-4}$ hydrocarbylamino.

In some embodiments, $R^1$ is —$SF_4$—X'—(Ar')$_{n'}$—$R^{2'}$, X' is the same as X, n' is the same as n, Ar' and Ar, where present, are the same, and $R^{2'}$ is the same as $R^2$.

In some embodiments, n is 0. In some embodiments, n is 1.

In some embodiments, n' is 0. In some embodiments, n' is 1.

In some embodiments, Ar is absent.
In some embodiments, Ar is phenyl.

In certain embodiments, the compound of Formula (I) is a compound of Formula (IA)-(IC), where $R^2$ is attached to Ar para, meta, or ortho to X.

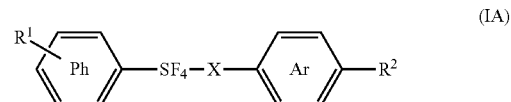

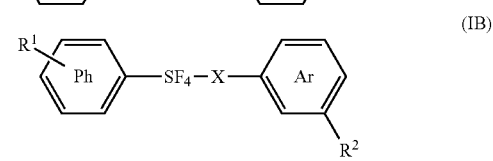

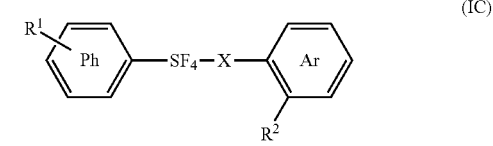

Ar is optionally substituted by up to four substituents (i.e., zero, one, two, three, or four substituents) in addition to $R^2$. In some embodiments, the up to four substituents in addition to $R^2$ on the Ar ring are different. In some embodiments, the up to four substituents in addition to $R^2$ on the Ar ring are the same.

In some embodiments, there are up to three substituents in addition to $R^2$ on the Ar ring. In some embodiments, the up to three substituents on Ar in addition to $R^2$ are independently selected from halogen, nitro, trifluoromethyl, and $C_{1-4}$ hydrocarbyl.

In some embodiments, Ar' is absent.
In some embodiments, Ar' is phenyl.

In certain embodiments, the compound of Formula (I) is a compound of Formula (IX)-(IZ), wherein $R^1$ is —$SF_4$—X'—(Ar')$_{n'}$—$R^{2'}$, and $R^{2'}$ is attached to Ar' para, meta, or ortho to X'.

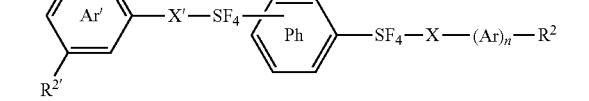

-continued

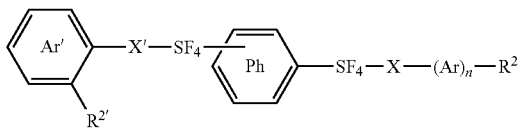
(IZ)

Ar' is optionally substituted by up to four substituents (i.e., zero, one, two, three, or four substituents) in addition to $R^{2'}$. In some embodiments, the up to four substituents in addition to $R^{2'}$ on the Ar' ring are different. In some embodiments, the up to four substituents in addition to $R^{2'}$ on the Ar' ring are the same.

In some embodiments, there are up to three substituents in addition to $R^{2'}$ on the Ar' ring. In some embodiments, the up to three substituents on Ar' in addition to $R^{2'}$ are independently selected from halogen, nitro, trifluoromethyl, and $C_{1-4}$ hydrocarbyl.

In another aspect, the invention provides a device comprising a compound of Formula (I).

In certain embodiments, the invention relates to an electro-optical display device, for example, a liquid crystal display (LCD) comprising a compound of Formula (I).

In another aspect, the invention provides a process for the preparation of a compound of Formula (I).

Chlorotetrafluorosulfanes may be prepared by any acceptable method known in the art. For example, preparation of the aryl chlorotetrafluorosulfane by reaction of a substituted aryl sulfide with chlorine in the presence of KF is a selective process that is not prone to oxidative decomposition processes. The substituted aryl sulfides can include additional substituents such as $CF_3$, $SF_5$, or halogens, which may amplify the induced molecular dipole.

In various embodiments, the aryl chlorotetrafluorosulfanes so prepared may be coupled with a wide variety of reactant partners including those that are electron-rich, thereby amplifying significantly the associated molecular dipole that may contribute to enhanced mesogenic performance.

In certain embodiments, the invention relates to preparing aryltetrafluorosulfane intermediates that bear a reactive functional group amenable to further transformations such as esterification, coupling, or reduction, that might be helpful for incorporation of the mesogenic moeity into a substrate where the crystallinity may be more easily modulated in the presence of adverse environmental effects such as extremes of temperature, that frequently limit liquid crystalline behavior. The coupling strategy may enable the preparation of very linear molecules, which could contribute to maximizing the dipolar effect.

In certain embodiments, the processes of the present invention are scalable, and/or do not require the use of particularly hazardous or reactive reagents.

In some embodiments, the invention relates to a process for the preparation of a compound of Formula (I) comprising reacting a compound of the formula:

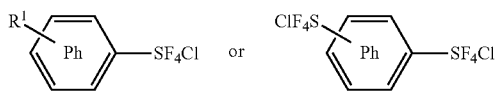

with an alkene or alkyne compound of the formula:

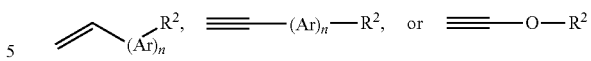

wherein Ph, Ar, n, $R^1$, and $R^2$ are as defined above, and optionally thereafter converting one compound of the Formula (I) into another compound of the Formula (I).

In some embodiments, the process of the invention is carried out in the presence of a free radical initiator. For example, in certain embodiments, the free radical initiator is a trialkyl borane, such as, e.g., $Et_3B$.

In some embodiments, the reaction is carried out in the presence of, e.g., dichloromethane as a solvent. In some embodiments, the reaction is carried out in the presence of a hydrocarbon solvent, such as, for example, a saturated hydrocarbon solvent (e.g., hexane).

Scheme A:

In some embodiments, the invention relates to a process for preparing a compound of the Formula (I-i) or (I-iiiA)

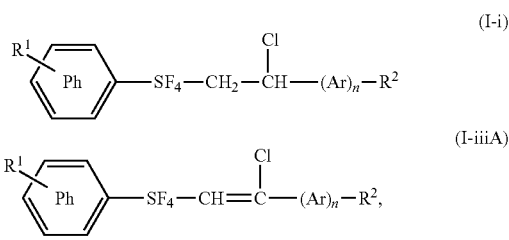

comprising reacting a compound of the formula:

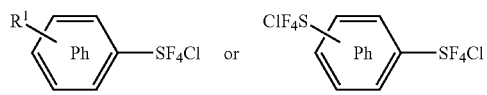

with an alkene or alkyne compound of the formula:

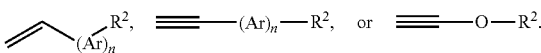

In some embodiments, the invention relates to a process according to Scheme A additionally comprising reacting a compound of Formula (I-i) with base to provide a compound of the Formula (I-iiiB):

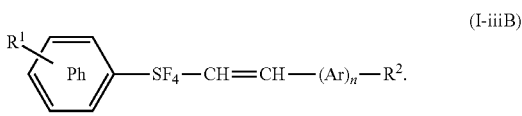

In some embodiments, the invention relates to a process according to Scheme A additionally comprising reacting a compound of Formula (I-iiiA) with base to provide a compound of the Formula (I-iv):

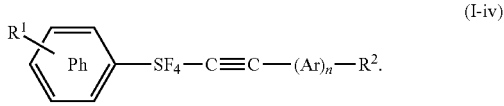

In some embodiments, the invention relates to a process according to Scheme A, wherein the compound of Formula (I-iiiA) is a compound of Formula (I-iiiC):

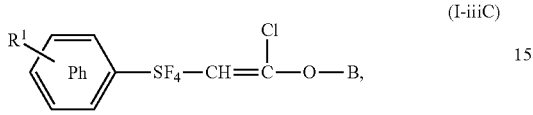

wherein B is as defined above, the process additionally comprising hydrolizing the compound of Formula (I-iiiC) to provide a compound of the Formula (I-iiA):

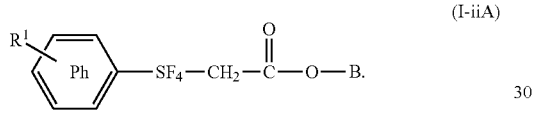

In some embodiments, hydrolizing is performed under acidic conditions. In certain embodiments, hydrolizing is performed under mild acidic conditions, for example, mildly acidic conditions (e.g., using silica gel).

EXAMPLES

The invention will now be illustrated, but not limited, by reference to the specific embodiments described in the following examples.

General

Melting points were measured by Mel-TEMP® capillary melting point apparatus.

$^1$H and $^{13}$C NMR spectra were recorded using Bruker® 400 MHz spectrometer and chemical shifts are reported in δ (ppm) and referenced to the residual CHCl$_3$ or C$_6$H$_6$ signal. $^1$H and $^{13}$C NMR data are tabulated as follows: chemical shift, multiplicity (singlet=s, d=doublet, t=triplet, q=quartet, p=pentet, m=multiplet), coupling constant, number of proton or carbon and atomic assignment. The C, H, and N elemental analysis was performed on a Carlo Erba CHN Analyzer (Complete Analysis Laboratories, Inc., Parsippany, N.J., USA), Materials Unless otherwise noted, commercial reagents were purchased from Sigma Aldrich, and Alpha Aesar, and other commercial suppliers, and were used as received. Chloroform-d (D, 99.8%)+(0.05% v/v TMS) and benzene-d6 (D, 99.8%)+ (0.05% v/v TMS) was purchased from Cambridge Isotope Laboratories, Inc.

Atomic Assignment

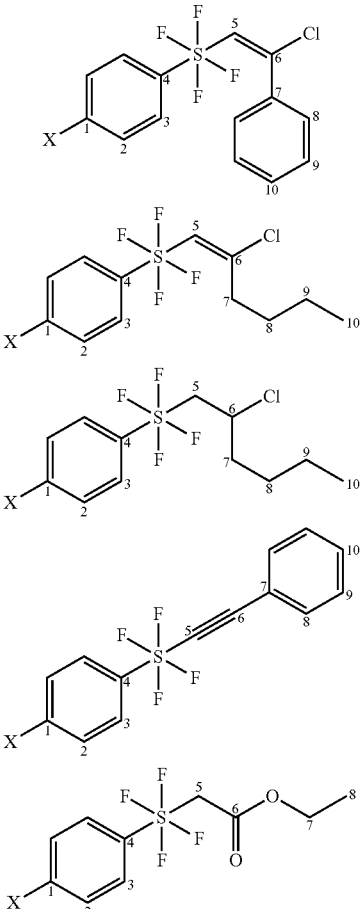

X = H, Cl, NO$_2$

The known compounds 3a-c were synthesized according to the literature:

Umemoto, T., et al., *Discovery of practical production processes for arylsulfur pentafluorides and their higher homologues, bis- and tris(sulfur pentafluorides): Beginning of a new era of "super-trifluoromethyl" arene chemistry and its industry*, Beilstein J. Org. Chem. 2012, 8, 461-471.
Umemoto et al., WO 2010/022001 A1 (Feb. 25, 2010).
Umemoto, U.S. 2010/0130790 A1 (May 27, 2010).
Umemoto, WO 2010/033930 (Mar. 25, 2010).
Umemoto et al., WO 2009/114409 A2 (Sep. 17, 2009).
Umemoto, U.S. 20080234520 A1 (Sep. 25, 2008).

[(E)
2-Chloro-2-phenylethenyl]phenyltetrafluorosulfane
(Example 1a)

To a stirred solution of Et$_2$O (1.5 mL) and 3a (150 mg, 0.680 mmol, 1 eq), was added (104 mg, 1.02 mmol, 1.5 eq) phenylacetylene, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture was quenched with 3.0 mL of saturated sodium bicarbonate and extracted twice with diethyl ether, the organic phase was dried over MgSO$_4$ and concentrated under reduced pressure to give a yellow solid, which was purified by crystallization from pentane for overnight at −20° C. to give 1a as a clear crystalline solid (48.0 mg, 22% yield); mp: 73-75° C.; $^1$H NMR (400 MHz, CDCl$_3$): 7.63 (dt, J=7.1 Hz, 2.0 Hz, 2H, H3), 7.48-7.28 (m, 8H, H1, H2, H8, H9, H10), 7.22 (p, J=8.3 Hz, 1H, H5); $^{13}$C NMR (100 MHz, CDCl$_3$): δ$_C$ (ppm)=160.4 (p, J=23.7 Hz, 1C, C4), 144.7 (p, J=30.0 Hz, 1C, C5), 138.2 (p, J=8.0 Hz, 1C, C6), 137.2 (s, 2C, C10), 130.4 (t, 0.7 Hz, 2C, C2), 129.3 (s, 1C, C8) 128.2 (p, J=1.8 Hz 2C, C7), 128.2 (s, 1C, C1), 128.1 (s, 2C, C9), 125.9 (p, J=5.3 Hz, 2C, C3). $^{19}$F NMR (376 MHz, CDCl$_3$) δ$_F$ (ppm)=70.4 (d, 8.4 Hz); Anal. Calcd for C14H11ClF4S: C, 52.10; H, 3.44. Found: C, 51.82; H: 3.55.

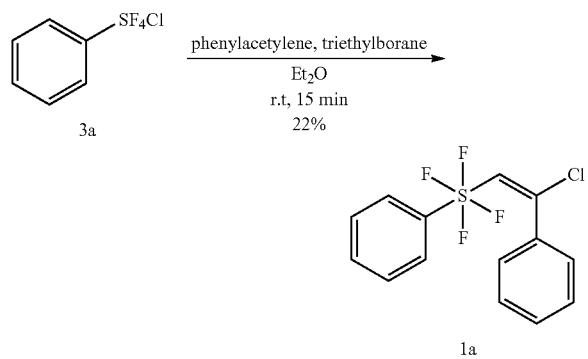

FIG. 1 shows the structure of Example 1a as determined by single crystal X-ray diffraction.

[(E) 2-Chloro-2-phenylethenyl]p-chlorophenyltetrafluorosulfane (Example 1b)

To a stirred solution of Et$_2$O (2.0 mL) and 3b (200 mg, 0.784 mmol, 1 eq), was added (120 mg, 1.18 mmol, 1.5 eq) phenylacetylene, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture was quenched with 3 mL of saturated sodium bicarbonate and extracted twice with diethyl ether, the organic phase was dried over MgSO$_4$ and concentrated under reduced pressure to give a yellow solid, which was purified by crystallization from pentane for overnight at −20° C. to give 1b clear crystalline solid (251 mg, 90% yield); mp: 124-125° C.; $^1$H NMR (400 MHz, CDCl$_3$): 7.58-7.52 (dt, J=9.1 Hz, 2.2 Hz, 2H, H3), 7.47-737 (m, 5H, H8, H9, H10), 7.30-7.25 (d, J=9.3 Hz, 2H, H2), 7.19 (p, J=8.4 Hz, 1H, H5); $^{13}$C NMR (100 MHz, CDCl$_3$): δ$_C$ (ppm)=158.4 (p, J=25.2 Hz, 1C, C4), 144.3 (p, J=30.1 Hz, 1C, C5), 138.6 (7.8 Hz, 1C, C6), 137.0 (s, 1C, C10), 136.3 (p, J=1.0 Hz 1C, C1), 129.4 (s, 2C, C8), 128.3 (t, J=0.7 Hz, 2C, C2), 128.2 (p, J=1.7 Hz, 1C, C7), 128.2 (s, 2C, C9), 127.4 (p, J=5.3 Hz, 2C, C3); $^{19}$F NMR (376 MHz, CDCl$_3$) δ$_F$ (ppm)=71.2 (d, J=8.3 Hz, 4F); Anal. Calcd for C14H10Cl2F4S: C, 47.08; H, 2.82. Found: C, 47.16; H, 2.91.

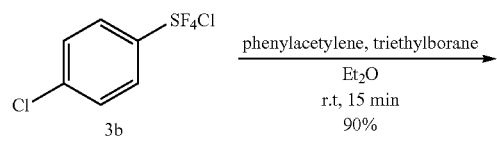

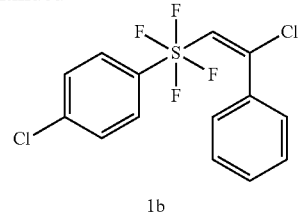

FIG. 2 shows the structure of Example 1b as determined by single crystal X-ray diffraction.

[(E) 2-Chloro-2-phenylethenyl]p-nitrophenyltetrafluorosulfane (Example 1c)

To a stirred solution of Et$_2$O (3.0 mL) and 3c (300 mg, 1.13 mmol, 1 eq), was added (173 mg, 1.70 mmol, 1.5 eq) phenylacetylene, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture was quenched with 3 mL of saturated sodium bicarbonate and extracted twice with diethyl ether, the organic phase was dried over MgSO$_4$ and concentrated under reduced pressure to give a yellow solid, which was purified by crystallization from pentane for overnight at −20° C. to give 1c clear crystalline solid (322 mg, 78% yield); 116.3-117.3° C.; 1H NMR (400 MHz, CDCl$_3$): 8.16 (d, J=9.1 Hz, 2H, H3), 7.79 (d, J=9.1 Hz, 2H, H2), 746-737 (m, 5H, H8, H9, H10), 7.19 (p, J=4.8 Hz, 1H, H5); $^{13}$C NMR (100 MHz, CDCl$_3$): δ$_C$ (ppm)=163.7 (p, J=26.5 Hz, 1C, C4), 148.2 (p, J=0.8 Hz, 1C. C1), 143.5 (p, J=29.2 Hz, 1C, C5), 139.5 (p, J=7.9 Hz, 1C, C6), 136.7 (s, 1C, C10), 129.5 (s, 2C, C8), 128.2 (s, 2C, C9), 128.1 (p, J=1.8 Hz, 1C, C7), 127.5 (p, J=5.4 Hz 2C, C3), 123.6 (s, 2C, C2); $^{19}$F NMR (376 MHz, CDCl$_3$) δ$_F$ (ppm)=77.9 (d, J=8.6 Hz, 4F); Anal. Calcd for C14H10ClF4NO2S: C, 45.72; H, 2.74; N, 3.81. Found: C, 45.83; H, 2.35; N, 3.72.

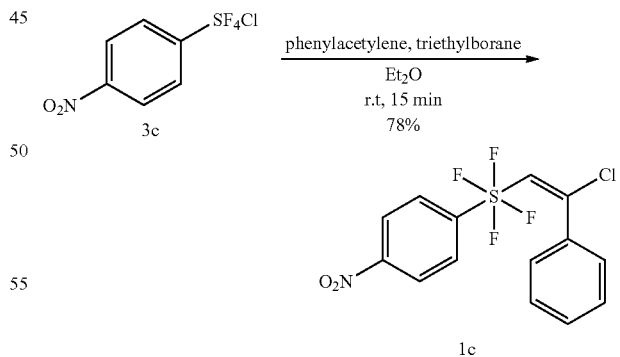

FIG. 3 shows the structure of Example 1c in a polar space as determined by single crystal X-ray diffraction, illustrating alignment of molecular dipoles, an assemblage believed to have utility, e.g., as in second harmonic generation or frequency doubling devices.

FIG. 4 shows the structure of Example 1c as determined by single crystal X-ray diffraction.

[(E) 2-Chloro-1-hexenyl]4-nitrophenyltetrafluorosulfane (Example 1d)

To a stirred solution of Et$_2$O (3.0 mL) and 3c (300 mg, 1.13 mmol, 1 eq), was added (139 mg, 1.70 mmol, 1.5 eq) 1-hexyne, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture was quenched with 3 mL of saturated Sodium bicarbonate and extracted twice with diethyl ether, the organic phase was dried over MgSO$_4$ and concentrated under reduced pressure to give a yellow oil, which was purified by column chromatography over silica gel with n-hexane-dichloromethane (8:2) to give a clear oil. X-ray quality crystals were obtained by crystallization from pentane for overnight at −20° C. to give 1d clear crystalline solid (258 mg, 66% yield); mp: 44.9-45.4° C.; $^1$H NMR (400 MHz, CDCl$_3$): $\delta_H$ (ppm)=8.26 (d, J=8.6 Hz, 2H, H3), 8.64 (d, J=9.2 Hz, 2H, H2), 6.85 (p, J=9.0 Hz, 1H, H5), 2.76 (t, J=7.9 Hz, 2H, H7), 1.65 (p, J=7.6 Hz, 2H, H8), 1.39 (m, J=7.4, 2H, H9), 0.94 (t, J=7.4 Hz, 3H, H10); $^{13}$C NMR (100 MHz, CDCl$_3$): $\delta_C$ (ppm)=164.4 (p, J=26.9 Hz, 1C, C4), 148.3 (p, J=1.0 Hz, 1C, C1), 144.7 (p, J=7.4 Hz, 1C, C6), 142.6 (p, J=28.0 Hz, 1C, C6), 127.6 (p, J=5.3 Hz, 2C, C3), 123.7 (s, 2C, C2), 36.0 (p, J=1.8 Hz, 1C, C7), 29.4 (s, 1C, C8), 22.3 (s, 1C, C9), 14.0 (s, 1C, C10); $^{19}$F NMR (376 MHz, CDCl$_3$): $\delta_F$ (ppm)=68.9 (d, 8.9 Hz, 4F); Anal. Calcd for C12H14ClF4NO2S: C, 41.45; H, 4.06; N, 4.03. Found: C, 41.39; H, 4.11; N, 3.96.

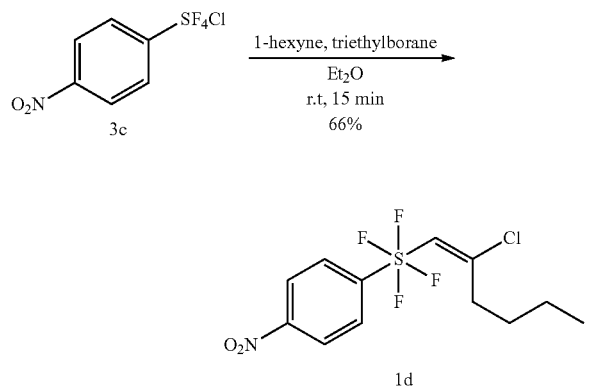

FIG. 5 shows the structure of Example 1d as determined by single crystal X-ray diffraction.

[(E) 2-Chloro-2-phenylethenyl]4-bromophenyltetrafluorosulfane (Example 1e)

To a stirred solution of Et$_2$O (1.0 mL) and 3d (1.0 g, 3.33 mmol, 1 eq), was added (380 mg, 3.70 mmol, 1.1 eq) phenylacetylene, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture of was quenched 3 mL of saturated sodium bicarbonate and extracted twice with diethyl ether, the organic phase was dried over MgSO$_4$ and concentrated under reduced pressure to give a yellow solid, which was purified by crystallization from pentane for overnight at −20° C. to give 1e clear crystalline solid (1.2 g, 88% yield); 101-106° C.; 1H NMR (400 MHz, CDCl$_3$): $\delta_H$ (ppm)=7.49-7.29 (m, 9H, H2, H3, H8, H9, H10), 7.16 (p, J=8.4 Hz, 1H, H5); $^{13}$C NMR (100 MHz, CDCl$_3$): $\delta_C$ (ppm)=158.99 (p, J=25.1 Hz, 1C, C4), 144.27 (p, J=30.4 Hz, 1C, C5), 138.69 (p, J=7.8 Hz, 1C, C6), 137.00 (s, 1C, C7), 131.25 (s, 1C, C8), 129.35 (s, 1C, C2), 128.17 (s, 1C, C10), 128.13 (s, 1C, C9), 127.59 (p, J=5 Hz, 1C, C3), 124.54 (s, 1C, C1); $^{19}$F NMR (376 MHz, CDCl$_3$) $\delta_F$ (ppm)=71.27 (d, J=8.3 Hz, 4F).

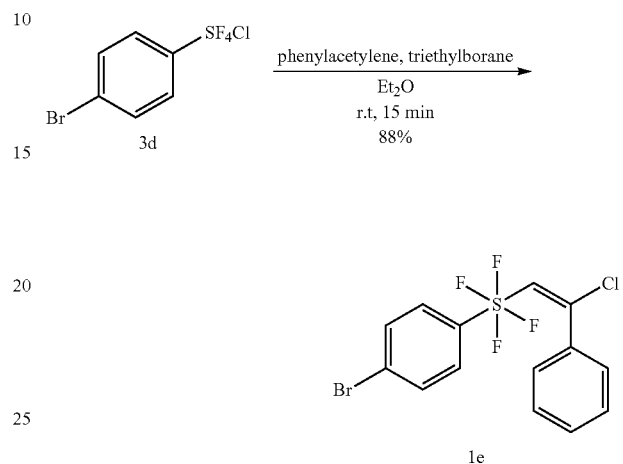

FIG. 6 shows the structure of Example 1e as determined by single crystal X-ray diffraction.

[(E) 2-Chloro-2-phenylethenyl]p-pentafluorophenyltetrafluorosulfane (Example 1f)

To a stirred solution of Et$_2$O (2.0 mL) and 3f (230 mg, 0.74 mmol, 1 eq), was added (90 mg, 0.76 mmol, 1.2 eq) phenylacetylene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the colorless oil was crystallized from pentane for overnight at −20° C. to give 1f clear crystalline solid (150 mg, 49% yield); $^{13}$C NMR (100 MHz, CDCl$_3$): $\delta_C$ (ppm)=147.67 (d, J=250.8 Hz, 1C, C4), 146.70 (d, J=257.9 Hz, 1C, C3), 142.34 (d, J=262.1 Hz, 1C, C1), 142.25 (p, J=54.2, 1C, C4), 140.89 (p, J=7.2 Hz, 1C, C6), 139.50-136.51 (d, m, 1C, C2), 136.42 (s, 1C, C7), 129.72 (s, 1C, C10), 128.25 (s, 1C, C8), 128.07 (s, 1C, C9).

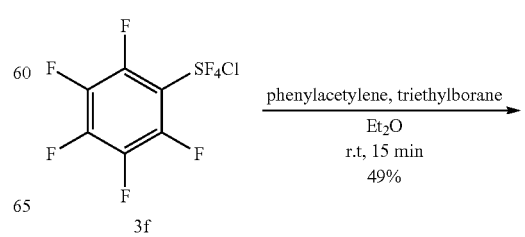

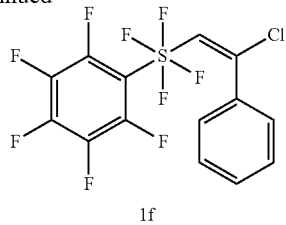

1f

[(E) 2-Chloro-2-phenylethenyl](3,5-(bis)trifluoromethylphenyl)tetrafluorosulfane (Example 1g)

To a stirred solution of Et$_2$O (2.0 mL) and 3e (230 mg, 0.64 mmol, 1 eq), was added (78 mg, 0.76 mmol, 1.2 eq) phenylacetylene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated Sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the colorless oil was crystallized from pentane for overnight at −20° C. to give 1g clear crystalline solid (44 mg, 15% yield); $^1$H NMR (400 MHz, CDCl$_3$): $\delta_H$ (ppm)=8.06 (s, 2H, H3), 7.89 (s, 1H, H1), 7.47-7.38 (m, 5H, H9, H10, H11), 7.20 (p, J=8.4 Hz, 1H, H5); $^{13}$C NMR (100 MHz, CDCl$_3$): $\delta_C$ (ppm)=160.42 (p, J=23.2 Hz, 1C, C4), 143.09 (p, J=28.5 Hz, 1C, C5), 140.02 (p, J=7.8 Hz, 1C, C6), 136.65 (s, 1C, C7), 132.08 (q, J=34.3 Hz, 1C, C2), 129.70 (s, 1C, C10), 128.34 (s, 1C, C9), 128.09 (s, 1C, C8), 126.76 (s, 1C, C1), 124.38 (s, 1C, C3), 121.32 (q, J=272.7 Hz, 1C, C11); $^{19}$F NMR (376 MHz, CDCl$_3$) $\delta_F$ (ppm)=71.27 (d, J=8.4 Hz, 4F), −63.42 (s, 3F).

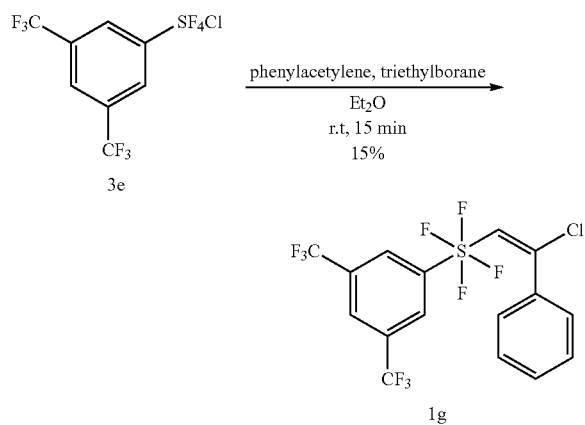

FIG. 7 shows the structure of Example 1g as determined by single crystal X-ray diffraction.

[2-Chloro-1-hexenyl]pentafluorophenyltetrafluorosulfane (Example 1h)

To a stirred solution of Et$_2$O (1.0 mL) and 3f (95 mg, 0.31 mmol, 1 eq), was added (38 mg, 0.46 mmol, 1.5 eq) phenylacetylene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the colorless oil (72 mg, 60% yield); $^1$H NMR (400 MHz, CDCl$_3$): $\delta_H$ (ppm)=4.56-4.45 (m, 1H, H6), 4.31-4.06 (m, 2H, H5), 2.02 (ddd, J=18.6, 9.4, 4.4 Hz, 1H, H7), 1.78 (dtd, J=14.0, 9.4, 4.7 Hz, 1H, H7), 1.66-1.29 (m, 5H, H9, H8), 0.94 (t, J=7.2 Hz, 3H, H10); $^{13}$C NMR (100 MHz, CDCl$_3$): $\delta_C$ (ppm)=147.65 (d, J=258.0 Hz, 1C, C1), 146.77 (d, J=252.4 Hz, 1C, C2), 143.02 (d, J=259.4 Hz, 1C, C3), 138.03 (d, J=257.3 Hz, 1C, C4), 81.43 (P, J=17.2 Hz, 1C, C5), 56.74 (P, J=4.7 Hz, 1C, C6), 37.42 (s, C7), 28.20 (s, J=14.9 Hz, C8), 22.10 (s, 1C, C9), 13.90 (s, J=14.8 Hz, 1C, C10).

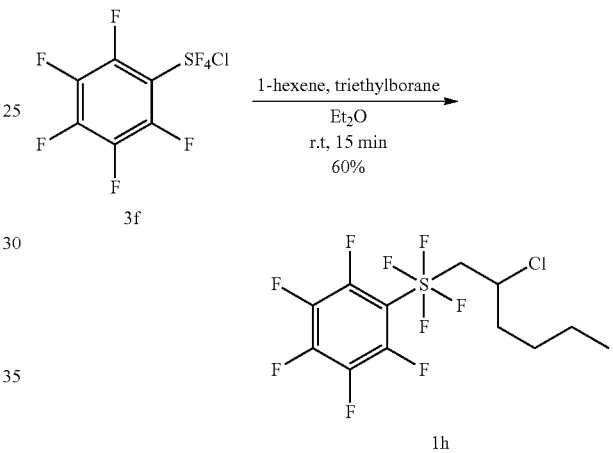

1h

[(E) 2-Chloro-2-p-trifluoromethylphenylethenyl]phenyltetrafluorosulfane (Example 1i)

To a stirred solution of Et$_2$O (1.0 mL) and 3a (100 mg, 0.45 mmol, 1 eq), was added (92 mg, 0.54 mmol, 1.2 eq) 4-Ethynyl-α,α,α-trifluorotoluene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the colorless oil was crystallized from pentane for overnight at −20° C. to give 1i clear crystalline solid (34 mg, 19% yield); $^1$H NMR (400 MHz, CDCl$_3$): $\delta_H$ (ppm)=7.66 (d, J=8.2 Hz, 2H, H9), 7.62 (d, J=7.7 Hz, 2H, H3), 7.57 (d, J=8.1 Hz, 2H, H8), 7.34 (p, J=7.1 Hz, 3H, H1), 7.25 (p, J=8.3 Hz, 1H, H5); $^{13}$C NMR (100 MHz, CDCl$_3$): $\delta_C$ (ppm)=160.14 (p, J=23.1 Hz, 1C, C4), 145.58 (p, J=31.4 Hz, 1C, C5), 140.74 (s, 1C, C1), 136.36 (p, J=7.9 Hz, 1C, C6), 131.33 (q, J=32.8 Hz, 1C, C10), 130.59 (s), 128.80 (s, 1C, C7), 128.36 (s, 1C, C8), 125.89 (p, J=5.1 Hz, 1C, C3), 125.28 (q, J=3.7 Hz, 1C, C9), 124.01 (q, J=270.1 Hz, 1C, C11); $^{19}$F NMR (376 MHz, CDCl$_3$) $\delta_F$ (ppm)=70.64 (d, J=8.3 Hz, 4F), −63.41 (s, 3F).

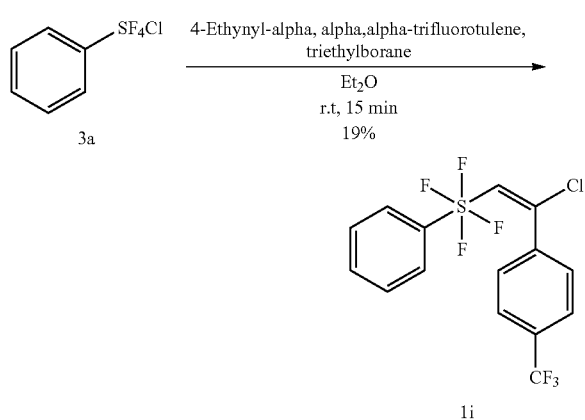

[(E) 2-Chloro-2-p-trifluoromethylphenylethenyl]p-chloro-phenyltetrafluorosulfane (Example 1j)

To a stirred solution of Et$_2$O (1.0 mL) and 3b (90 mg, 0.35 mmol, 1 eq), was added (66 mg, 0.39 mmol, 1.1 eq) 4-ethynyl-α,α,α-trifluorotoluene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated Sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the white solid crystallized from pentane for overnight at −20° C. to give 1j clear crystalline solid (41 mg, 27% yield); $^1$H NMR (400 MHz, CDCl$_3$): δ$_H$ (ppm)=7.57 (d, J=8.2 Hz, 2H, H2), 7.45 (d, J=9.2 Hz, 2H, H8), 7.45 (d, J=9.2 Hz, 2H, H3), 7.20 (d, J=8.7 Hz, 2H, H9), 7.12 (p, J=8.4 Hz, 1H, H5); $^{13}$C NMR (100 MHz, CDCl$_3$): δ$_C$ (ppm)=158.17 (p, J=25.0 Hz, 1C, C4), 145.23 (p, J=31.2, 1C, C5), 140.58 (s, 1C, C7), 136.81 (p, J=8.2 Hz, 1C, C6), 136.59 (s, 1C, C1), 131.44 (q, J=32.9 Hz, 1C, C10), 128.74 (s, 1C, C2), 128.39 (s, 1C, C8), 127.37 (p, J=5.2 Hz, 1C, C3), 125.32 (q, J=3.8 Hz, 1C, C9), 123.44 (q, J=272.6 Hz, 1C, C11); $^{19}$F NMR (376 MHz, CDCl$_3$) δ$_F$ (ppm)=71.47 (d, J=8.3 Hz, 4F), −63.43 (s, 3F).

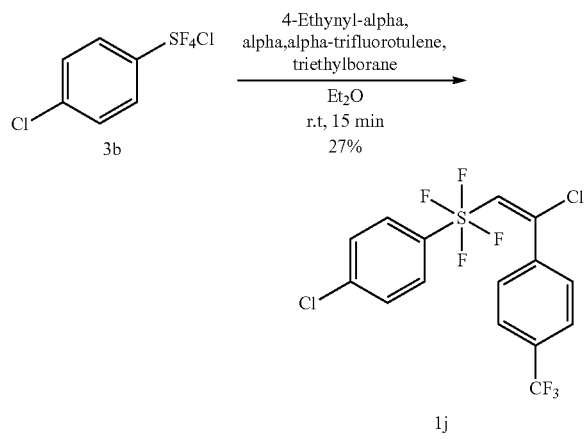

[(E) 2-Chloro-2-p-trifluoromethylphenylethenyl]p-nitro-phenyltetrafluorosulfane (Example 1k)

To a stirred solution of Et$_2$O (1.0 mL) and 3c (112 mg, 0.42 mmol, 1 eq), was added (79 mg, 0.46 mmol, 1.1 eq) 4-ethynyl-α,α,α-trifluorotoluene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated Sodium bicarbonate and extracted twice with diethyl ether, the organic phase was dried over MgSO$_4$ and concentrated under reduced pressure to give a yellow oil, which was purified by silica gel column chromatography (hexane alone to elude the product out) the white solid crystallized from pentane for overnight at −20° C. to give 1k clear crystalline solid (61 mg, 33% yield); 97-99° C.; $^1$H NMR (400 MHz, CDCl$_3$): δ$_H$ (ppm)=8.18 (d, J=8.9 Hz, 2H, H2), 7.79 (d, J=9.2 Hz, 2H, H3), 7.67 (d, J=8.2 Hz, 2H, H8), 7.55 (d, J=8.1 Hz, 2H, H9), 7.24 (p, J=8.4 Hz, 1H, H5); $^{13}$C NMR (100 MHz, CDCl$_3$): δ$_C$ (ppm)=163.55 (p, J=25.8 Hz, 1C, C4), 148.44 (s, 1C, C1), 144.46 (p, J=29.7 Hz, C5), 140.30 (s, 1C, C7), 137.67 (p, J=7.8 Hz, 1C, C6), 131.60 (q, J=32.8 Hz, 1C, C10), 128.67 (s, 1C, C2), 127.45 (p, J=5.1 Hz, 1C, C3), 125.40 (q, J=3.7 Hz, 1C, C9), 123.80 (q, J=272.8 Hz, 1C, C11); $^{19}$F NMR (376 MHz, CDCl$_3$) δ$_F$ (ppm)=71.10 (d, J=8.3 Hz, 4F), −63.47 (s, 3F).

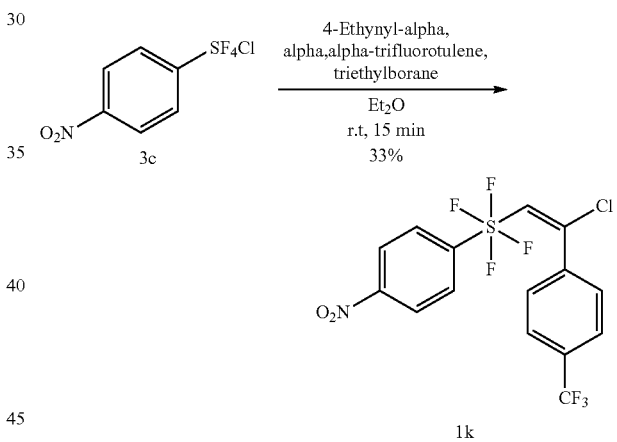

[(E) 2-Chloro-2-(p-trifluoromethylphenyl)ethenyl]4-bromophenyltetrafluorosulfane (Example 1l)

To a stirred solution of Et$_2$O (1.0 mL) and 3d (102 mg, 0.34 mmol, 1 eq), was added (64 mg, 0.38 mmol, 1.1 eq) 4-ethynyl-α,α,α-trifluorotoluene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched 3 mL of saturated Sodium bicarbonate and extracted twice with diethyl ether, the organic phase was dried over MgSO$_4$ and concentrated under reduced pressure to give a yellow solid, which was recrystallized from pentane for overnight at −20° C. to give 1l as a clear crystalline solid (92 mg, 58% yield); 112-113° C.; $^1$H NMR (400 MHz, CDCl$_3$): δ$_H$ (ppm)=7.66 (d, J=8.0 Hz, 2H, H2), 7.56 (s, 2H, H3), 7.50-7.42 (m, 4H, H8, H9), 7.22 (p, J=8.3 Hz, 1H, H5); $^{13}$C NMR (100 MHz, CDCl$_3$): δ$_C$ (ppm)=158.74 (p, J=24.9 Hz, 1C, C4), 145.19 (p, J=31.1 Hz, 1C, C6), 140.56 (s, 1C, C7), 136.79 (p, J=7.6 Hz, 1C, C6), 131.43 (q, J=32.8 Hz, 1C, C10), 131.41 (s, 1C, C2), 128.73 (s, C8), 127.56 (p, J=5.1 Hz, 1C, C3), 125.32 (q, J=3.7 Hz, 1C, C9), 124.83 (s, 1C, C1), 123.89 (q, J=272.4 Hz, 1C, C11); $^{19}$F NMR (376 MHz, CDCl$_3$) $\delta_F$ (ppm)=71.36 (d, J=8.2 Hz, 3F), −63.43 (s, 3F).

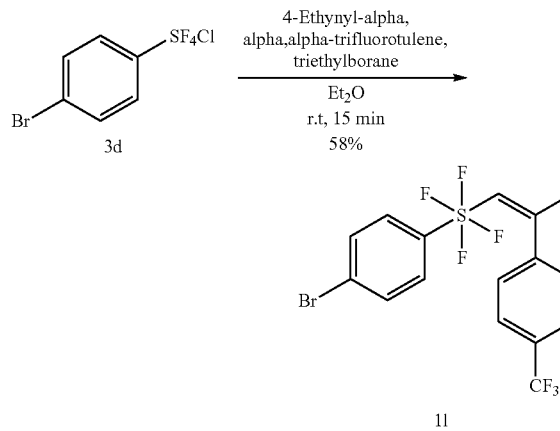

1,4{Bis[(E) 2-Chloro 2-phenylethenyl]tetrafluorosulfanyl}benzene (Example 1m)

To a stirred solution of Et$_2$O (1.0 mL) and 3g (54 mg, 0.15 mmol, 1 eq), was added (30 mg, 0.29 mmol, 0.99 eq) phenyl acetylene, and then a drop wise addition of triethylborane (1 M solution in hexane, 0.05 mL) via a syringe. The reaction was checked by $^{19}$F NMR, 15 minutes after the addition of triethylborane, which indicated a complete conversion to the product. The reaction mixture of was quenched mL of saturated sodium bicarbonate and extracted twice with diethyl ether, the organic phase was dried over MgSO$_4$ and concentrated under reduced pressure to give a beige solid, which was recrystallized from pentane/dichloromethane for overnight at −20° C. to give 1m as a clear crystalline solid (19 mg, 22% yield);

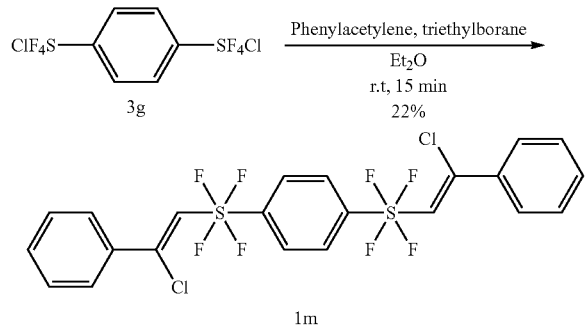

2-Chloro-1-hexenyl 4-nitrophenyltetrafluorosulfane (Example 2)

To a stirred solution of Et$_2$O (3.0 mL) and 3c (300 mg, 1.13 mmol, 1 eq), was added (143 mg, 1.70 mmol, 1.5 eq) 1-hexene, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture was quenched with 3 mL of saturated sodium bicarbonate and extracted twice with diethyl ether, the organic phase was dried over MgSO$_4$ and concentrated under reduced pressure to give a yellow oil, which was purified by column chromatography over silica gel with n-hexane-dichloromethane (8:2) to give 2 as a clear oil. X-ray quality crystals were obtained by crystallization from pentane for overnight at −20° C. to give clear crystalline solid (260 mg, 66% yield); $^1$H NMR (400 MHz, CDCl$_3$): $\delta_H$ (ppm)=8.24 (d, J=9.1 Hz, 2H, H3), 7.92 (d, J=9.3 Hz, 2H, H2), 4.53 (m, 1H, H6), 4.38-4.12 (m, 2H, H5), 2.11-2.00 (m, 1H, H7$_a$), 1.85-1.74 (m, 1H, H7$_b$), 1.66-1.29 (m, 4H, H8, H9), 0.94 (t, J=7.4 Hz, 3H, H10); $^{13}$C NMR (100 MHz, CDCl$_3$): $\delta_C$ (ppm)=164.6 (p, J=27.1 Hz, 1C, C4), 148.3 (m, 1C, C1), 127.6 (p, J=5.6 Hz, 2C, C3), 123.7 (s, 2C, C2), 83.2 (p, J=19.0 Hz, 1C, C5), 57.3 (p, J=5.3 Hz, 1C, C6), 37.5 (p, J=1.3 Hz, 1C, C7), 28.4 (s, 1C, C8), 22.1 (s. 1C, C9), 14.0 (s, 1C. C10); $^{19}$F NMR (376 MHz, CDCl$_3$) $\delta_F$ (ppm)=64.4 (t, 8.4 Hz, 4F); Anal. Calcd for: C12H16ClF4NO2S: C, 41.21; H, 4.61; N, 4.00. Found: C, 41.32; H, 4.61; N, 4.20.

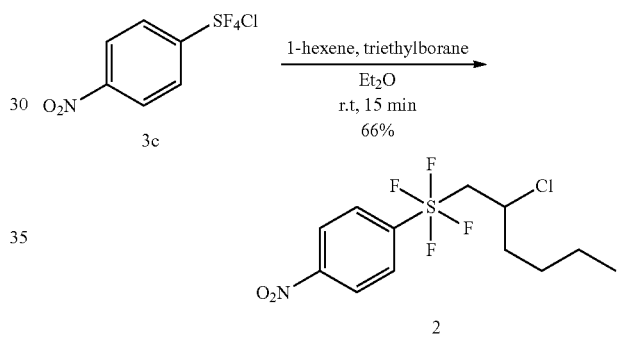

FIG. 8 shows the structure of Example 2 as determined by single crystal X-ray diffraction.

(Phenylethynyl)phenyltetrafluorosulfane (Example 6a)

To a stirred solution of DMSO (9 mL), and 1a (56.0 mg, 0.174 mmol, 1 eq), was added (72.8 mg, 1.74 mmol, 10 eq) lithium hydroxide mono hydrate, after 5 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give a yellow solid. The crude material was purified by crystallization from pentane for overnight at −20° C. to give 6a, a clear crystalline solid (48.5 mg, 97%) mp: 102-103° C.; $^1$H NMR (400 MHz, CDCl$_3$): $\delta_H$ (ppm)=7.81 (d, J=8.4 Hz, 2H, H3), 7.60 (d, J=7.42 Hz, 2H, H2), 7.49-7.35 (m, 6H, H1, H8, H9, H10); $^{13}$C NMR (100 MHz, CDCl$_3$): $\delta_C$ (ppm)=159.6 (p, J=22.5 Hz, 1C, C4), 132.6 (p, J=1.7 Hz, 2C, C8), 130.8 (s, 1C, C1), 130.3 (s, 1C, C10), 128.6 (s, 2C, C9), 128.5 (t, J=0.7 Hz, 1C, C7), 126.0 (p, J=5.1 Hz, 2C, C3), 119.0 (p, J=1.8 Hz, 1C, C7), 95.5 (p, J=54.7 Hz, 1C, C5), 72.6 (p, J=10.1 Hz, 1C, C6); $^{19}$F NMR (376 MHz, CDCl$_3$) $\delta_F$ (ppm)=87.36 (s, 4F); Anal. Calcd for: C14H10F4S: C, 58.73; H, 3.52. Found: C, 59.02; H, 3.30.

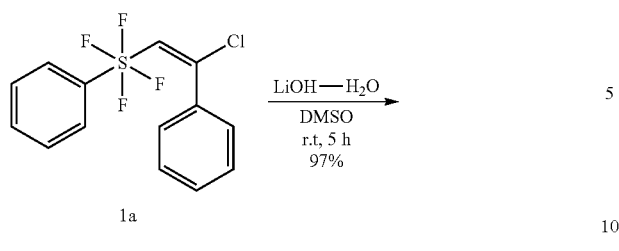

1a

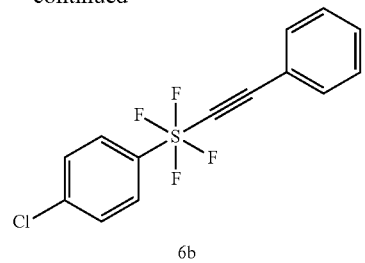

6b

FIG. 10 shows the structure of Example 6b as determined by single crystal X-ray diffraction.

(Phenylethynyl)4-nitrophenyltetrafluorosulfane (Example 6c)

To a stirred solution of DMSO (9 mL), and 1c (106 mg, 0.296 mmol, 1 eq), was added (121 mg, 2.96 mmol, 10 eq) lithium hydroxide mono hydrate, after 5 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give a yellow solid. The crude material was purified by crystallization from pentane for overnight at −20° C. to give 6c, a clear crystalline solid (77.0 mg, 81%); mp: 115-119° C.; $^1$H NMR (400 MHz, CDCl$_3$): δ$_H$ (ppm)=8.29 (d, J=8.9 Hz, 2H, H3), 7.98 (d, J=9.3 Hz, 2H, H2), 7.60 (d, J=7.3 Hz, 2H, H8), 7.50-7.37 (m, 3H, H9, H10); $^{13}$C NMR (100 MHz, CDCl$_3$): δ$_C$ (ppm)=163.1 (p, J=25.2 Hz, 1C, C4), 148.6 (m, 1C, C1), 132.7 (p, J=1.6 Hz, 2C, C8), 130.7 (s, 1C, C10), 128.8 (s, 2C, C9), 127.6 (p, J=5.0 Hz, 2C, C3), 123.9 (s, 2C, C2), 118.5 (m, 1C, C7), 94.3 (p, J=52.0 Hz, 1C, C5), 74.1 (p, J=10.1 Hz, 1C, C6); $^{19}$F NMR (376 MHz, CDCl$_3$) δ$_F$ (ppm)=87.59 (s, 4F); Anal. Calcd for: C14H9F4NO2S: C, 50.76; H, 2.74; N, 4.23. Found: C, 50.77; H, 2.42; N, 4.10.

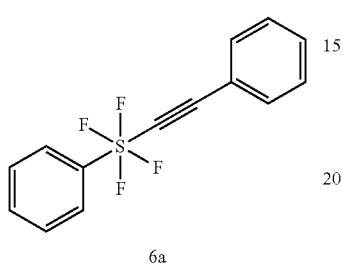

6a

FIG. 9 shows the structure of Example 6a as determined by single crystal X-ray diffraction.

(Phenylethynyl)4-chlorophenyltetrafluorosulfane (Example 6b)

To a stirred solution of DMSO (17 mL), and 1b (37 mg, 0.104 mmol, 1 eq), was added (21.7 mg, 0.518 mmol, 5 eq) lithium hydroxide mono hydrate, after 5 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give a yellow solid. The crude material was purified by crystallization from pentane for overnight at −20° C. to give 6b, a clear crystalline solid (33.0 mg, 99%); mp: 77.1-77.9° C.; 1H NMR (400 MHz, CDCl$_3$): δ$_H$ (ppm)=7.72 (d, J=9.0 Hz, 2H, H3), 7.58 (d, J=7.1 Hz, 2H, H2), 7.47-7.34 (m, 5H, H8, H9, H10); $^{13}$C NMR (100 MHz, CDCl$_3$): δ$_C$ (ppm)=157.6 (p, J=24.4, 1C, C4), 136.8 (p, J=1.0 Hz, 1C, C1), 136.6 (p, J=1.7, 2C, C8), 130.4 (s, 1C, C10), 128.7 (s, 2C, C9), 128.6 (s, 2C, C2), 127.5 (p, J=5.0 Hz, 2C, C3), 118.8 (p, J=1.9 Hz, 1C, C7), 95.1 (p, J=54.0 Hz, 1C, C5). 73.1 (p, J=10.0 Hz, 1C, C6); $^{19}$F NMR (376 MHz, CDCl$_3$) δ$_F$ (ppm)=88.09 (s, 4F); Anal. Calcd for: C14H9ClF4S, C, 52.43; H, 2.83. Found: C, 52.41; H, 3.30.

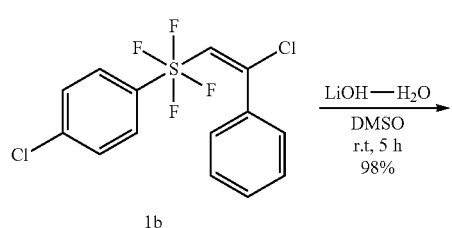

1b

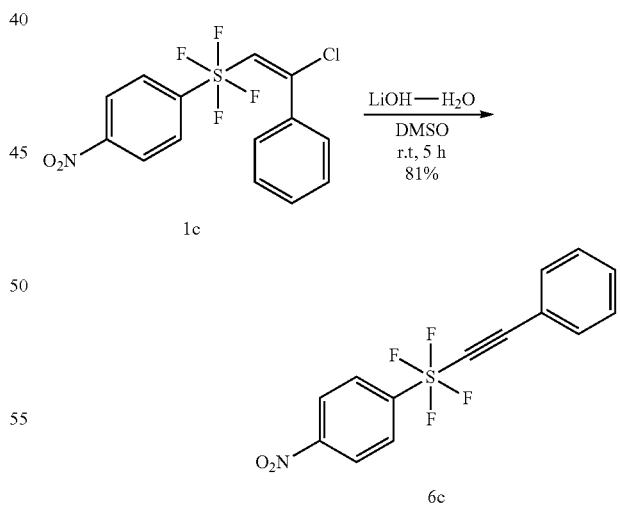

6c

FIG. 11 shows the structure of Example 6c as determined by single crystal X-ray diffraction.

Hexynyl 4-nitrophenyltetrafluorosulfane (Example 6d)

To a stirred solution of DMSO (5 mL), and 1d (167 mg, 0.480 mmol, 1 eq), was added (201 mg, 4.80 mmol, 10 eq)

lithium hydroxide mono hydrate, after 5 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give a yellow oil. The crude material was purified by column chromatography over silica gel with n-hexane-dichloromethane (8:2) to give 6d as a clear oil. X-ray quality crystals were obtained by crystallization from pentane for overnight at −20° C. to give clear crystalline solid (130 mg, 87%); $^1$H NMR (400 MHz, CDCl$_3$): $\delta_H$ (ppm)=8.25 (d, J=8.9 Hz, 2H, H3), 7.91 (d, J=9.4 Hz, 2H, H2), 2.35 (9 peaks, J=3.6 Hz, 2H, H7), 1.6 (p, J=7.5 Hz, 2H, H8), 1.48 (p, J=7.5 Hz, 2H, H9), 0.95 (t, J=7.4, 3H, H10); $^{13}$C NMR (100 MHz, CDCl$_3$): $\delta_C$ (ppm)=163.4 (p, J=25.9 Hz, 1C, C4), 148.4 (m, 1C, C1), 127.5 (p, J=5.1 Hz, 2C, C3), 123.7 (s, 2C, C2), 86.4 (p, J=51.5 Hz, 1C, C5), 76.3, 9.8 Hz, 1C, C6), 29.5 (p, J=1.3 Hz, 1C, C7), 22.0 (s, 1C, C8), 17.3 (p, J=1.3 Hz 1C, C9), 13.5 (s, 1C, C10); $^{19}$F NMR (376 MHz, CDCl$_3$) $\delta_F$ (ppm)=88.03 (t, 3.8 Hz, 4F); Anal. Calcd for: C12H13F4NO2S: C, 46.30; H, 4.21; N, 4.50. Found: C, 46.35; H, 4.28; N, 4.46.

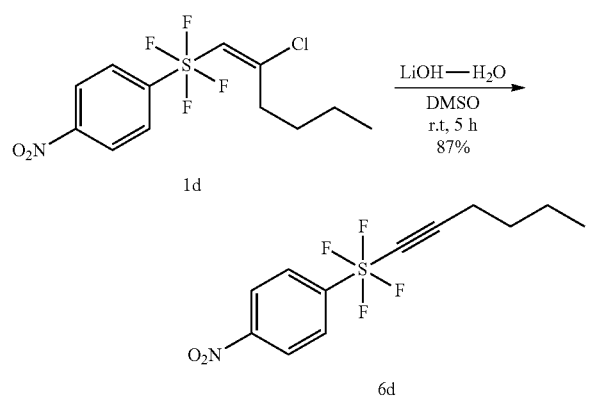

FIG. 12 shows the structure of Example 6d as determined by single crystal X-ray diffraction.

1,4[Bis-(tetrafluorosulfanylphenylethynyl)]benzene (Example 6e)

To a stirred solution of DMSO (2 mL), and 1m (167 mg, 0.034 mmol, 1 eq), was added (21 mg, 0.5 mmol, 15 eq) lithium hydroxide mono hydrate, after 18 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give beige solid. was purified by column chromatography over silica gel with n-hexane-dichloromethane (8:2) to give 6d as a clear oil. X-ray quality crystals were obtained by crystallization from pentane for overnight at −20° C. to give clear crystalline solid; which was recrystallized from pentane/Dichloromethane for overnight at −20° C. to give 6e as a clear crystalline solid (14 mg, 84% yield); $^1$H NMR (400 MHz, CDCl$_3$): $\delta_H$ (ppm)=7.86 (s, 4H, H1), 7.60 (d, J=7.1 Hz, 4H, H6), 7.43 (dq, J=14.6, 7.3 Hz, 6H, H7, H8); $^{13}$C NMR (100 MHz, CDCl$_3$): $\delta_C$ (ppm)=160.11 (p, J=24.5 Hz, 2C, C2), 132.67 (s, 2C, C6), 130.54 (s, 2C, C8), 128.71 (s, 4C, C7), 126.44 (p, 4C, C1), 118.78 (s, 2C, C5), 94.81 (p, J=4.9 Hz, 2C, C3), 73.58 (p, J=8.5 Hz, 2C, C4); $^{19}$F NMR (376 MHz, CDCl$_3$) $\delta_F$ (ppm)=87.55 (s, 4F).

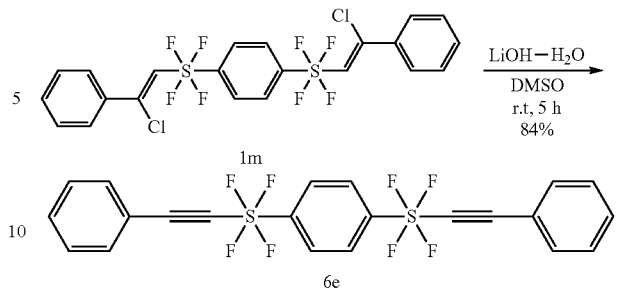

FIG. 13 shows the structure of Example 6e as determined by single crystal X-ray diffraction.

1-Hexenyl 4-nitrophenyltetrafluorosulfane (Example 7)

To a stirred solution of DMSO (8 mL), and 2 (210 mg, 0.600 mmol, 1 eq), was added (252 mg, 6.00 mmol, 10 eq) lithium hydroxide mono hydrate, after 5 hours the reaction was checked by $^{19}$F NMR which indicated a complete conversion to the product, the reaction mixture was poured onto ice and extracted with diethyl ether. The ethereal phase was dried over magnesium sulfate and concentrated under reduced pressure to give a yellow oil. The crude material was purified by crystallization from pentane for overnight at −20° C. to give 7 as a clear crystalline solid (184 mg, 98%); mp: 34-35° C.; $^1$H NMR (400 MHz, CDCl$_3$): $\delta_H$ (ppm)=8.23 (d, J=8.9 Hz, 2H, H3), 7.93 (d, J=9.2 Hz, 2H, H2), 6.65 (7 peaks, J=7.0 Hz, 1H, H5), 6.50 (7 peaks, J=7.0 Hz, 1H, H6), 2.18 (d, J=6.2 Hz, 2H, H7), 1.53-1.32 (m, 4H, H8, H9), 0.93 (t, J=7.4 Hz, 3H, H10); $^{13}$C NMR (100 MHz, CDCl$_3$): $\delta_C$ (ppm)=165.0 (p, J=28.0 Hz, 1C, C4), 148.1 (m, 1C, C1), 146.4 (p, J=25.5 Hz, 1C, C5), 135.8 (p, J=8.0 Hz, 1C, C6), 127.6 (p, J=5.5 Hz, 2C, C3), 123.6 (s, 2C, C2), 30.3 (t, J=1.0 Hz 1C, C7), 30.1 (s, 1C, C8), 22.3 (s, 1C, C9), 13.9 (s, 1C, C10); $^{19}$F NMR (376 MHz, CDCl$_3$) $\delta_F$ (ppm)=64.66 (d, 6.9 Hz, 4F); Anal. Calcd for: C12H15F4NO2S: C, 46.00; H, 4.83; N, 4.47. Found: C, 46.02; H, 4.85; N, 4.43.

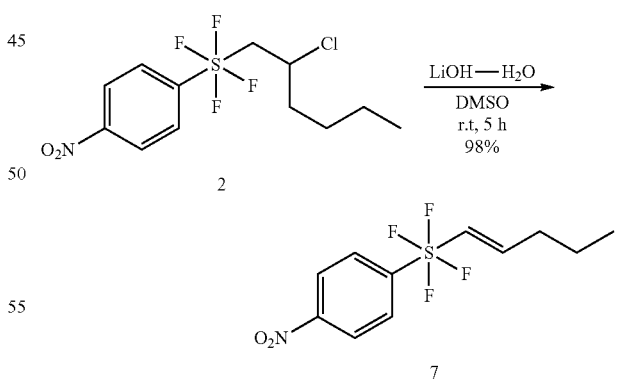

[(E) 1-Chloro-2-ethoxyethenyl]4-nitrophenyltetrafluorosulfane (Example 1n)

To a stirred solution of Et$_2$O (1.5 mL) and 3c (150 mg, 0.56 mmol, 1 eq), was added (47 mg, 0.68 mmol, 1.2 eq) ethyl ethynyl ether, and then a drop wise addition of triethylborane (1 M solution in hexane, 0.1 mL) via a syringe. The reaction was checked by $^{19}$F NMR, 15 minutes after the addition of triethylborane, which indicated a complete conversion to the product. The reaction mixture of was quenched 3.0 mL of saturated sodium bicarbonate and extracted twice with diethyl ether, the organic phase was dried over $MgSO_4$ and concentrated under reduced pressure to give the crude product as a yellow oil (153 mg, 81% yield) the unstable adduct was hydrolyzed to compound 8 after silica gel column chromatography.

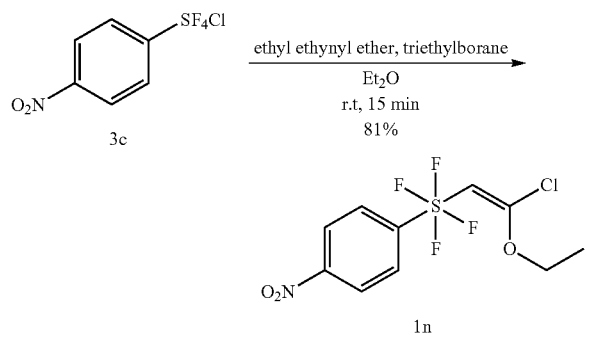

Ethyl 4-nitrophenyltetrafluorosulfanylacetate
(Example 8)

To a stirred solution of dichloromethane (6 mL) and 1n (360 mg, 1.07 mmol, 1 eq) was added silica gel (1.0 g, 16.6 mmol, 15.5 eq) the mixture was stirred for one hour room temperature and the reaction was checked by $^{19}$F NMR which indicated a complete consumption of the starting material. The reaction mixture was filtered and evaporated; the crude product was purified by silica column chromatography (4:6) dichoromethane:hexane to give the pure product 8. X-ray quality crystals were obtained by crystallization overnight at −20 from pentane (75.0 mg, 22% yield); mp: 57.8-58.0° C.; $^{1}$H NMR (400 MHz, $CDCl_3$): $\delta_H$ (ppm)=8.25, (d, J=9.2 Hz, 2H, H3), 7.93 (d, J=9.2 Hz, 2H, H2), 4.53 (p, J=7.9 Hz, 2H, H5), 4.29 (q, J=7.1 Hz, 2H, H7), 1.34 (t, J=7.1 Hz, 3H, H8); $^{13}$C NMR (100 MHz, $CDCl_3$): $\delta_C$ (ppm)=163.3 (p, J=25.9 Hz, 1C, C4), 163.0 (p, J=5.1 Hz, 1C, C6), 148.2 (s, 1C, C1), 127.1 (p, J=5.4 Hz, 2C, C3), 123.4 (s, 2C, C2), 76.2 (p, 23.1 J=Hz, 1C, C5), 62.1 (s, 1C, C7), 13.8 (s, 1C, C8); $^{19}$F NMR (376 MHz, $CDCl_3$) $\delta_F$ (ppm)=74.3 (t, J=8.0 Hz, 4F); Anal. Calcd for C10H11F4NO4S: C, 37.86; H, 3.49; N, 4.41. Found: C, 37.92; H, 3.50; N, 4.35.

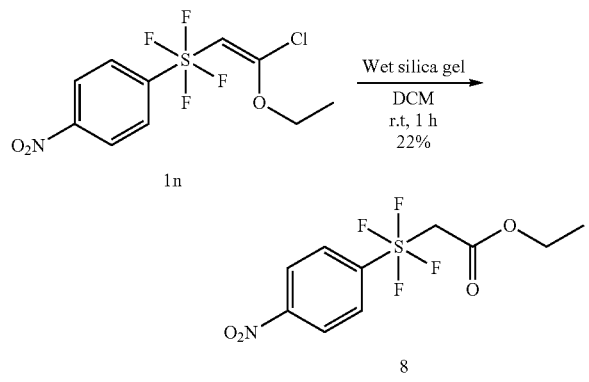

FIG. 14 shows the structure of Example 8 as determined by single crystal X-ray diffraction.

Materials with high dielectric anisotropy, solubility, and/or chemically robust behavior to avoid interactions with impurities or photochemical degradation are useful in liquid crystal design. [Kirsch, P.; Binder, W.; Hahn, A.; Jahrling, K.; Lenges, M.; Lietzau, L.; Maillard, D.; Meyer, V.; Poetsch, E.; Ruhl, A.; Unger, G.; Frolich, R. Super-fluorinated liquid crystals: towards the limits of polarity. Eur. J. Org. Chem. 2008, 3479-3487.] The $\lambda^6$-tetrafluorosulfanyl group suggests a novel approach to the preparation of compounds with those properties.

Twisted nematic liquid crystals require positive dielectric anisotropy aligned along the long molecular axis of the crystal for effective switching. The unique octahedral geometry around a $\lambda^6$-tetrafluorosulfanyl group constrains the desirable linear architecture of the molecule as can be seen in FIGS. 9-11, examples 6a-c.

It is has been postulated that intrinsically fluorinated polar bridges coupled with extremely polar terminal fluorinated end groups may be a nearly optimal solution for the design of high performance liquid crystals. [Kirsch, P.; Binder, W.; Hahn, A.; Jahrling, K.; Lenges, M.; Lietzau, L.; Maillard, D.; Meyer, V.; Poetsch, E.; Ruhl, A.; Unger, G.; Frolich, R. Super-fluorinated liquid crystals: towards the limits of polarity. Eur. J. Org. Chem. 2008, 3479-3487.] Example 1g, is illustrative of the preparation of an intermediate to achieve a more polarized structure, e.g., because the example is a precursor to the corresponding alkyne. In example 1h, the fluorines ortho to the pentafluorosulfanyl group displace the fluorines of the tetrafluorosulfanyl group. In this case the reduction in the C—S—F bond angle as observed by crystallography, with the fluorines displaced toward the aromatic ring, is consistent with predicted behavior and should therefore increase the dipole moment of the compound. [Kirsch, P.; Hahn, A. Liquid crystals based on hypervalent sulfur fluorides: Exploring the steric effects of ortho-fluorine substituents. Eur. J. Org. Chem. 2005, 3095-3100.] This property would lend to the $SF_4$ bridge characteristics associated with the $CF_2O$ linkage employed in high performance liquid crystal compositions, thus suggested that the compound would be highly useful in liquid crystal display applications. [See Matsushita, T.; Koseki, S. Theoretical Study on Mesogenic Core Structures of Nematic Liquid Crystalline Compounds. J. Phys. Chem. B 2005, 109, 13493-13498.]

In addition to dielectric anisotropy, effective liquid crystals optimally also have low rotational viscosity to improve the rapidity of switching. It is well known that parallel alignments of the aromatic rings of potential liquid crystals predict low rotational viscosity in the bulk, and hence lower clearing points. [Matsushita, T.; Koseki, S. Theoretical Study on Mesogenic Core Structures of Nematic Liquid Crystalline Compounds. J. Phys. Chem. B 2005, 109, 13493-13498.] The stronger intermolecular interactions that are derived from T-shaped packing of aromatic rings lead to higher viscosity and thereby higher clearing points. [Matsushita, T.; Koseki, S. Theoretical Study on Mesogenic Core Structures of Nematic Liquid Crystalline Compounds. J. Phys. Chem. B 2005, 109, 13493-13498.] From packing diagrams of single crystal x-ray diffraction studies of examples 6a-c (see FIGS. 9-11), it can be seen that T-shaped interactions are minimized by the constraints imposed by the $SF_4$ unit suggesting that switching will not likely be impeded by T-shaped interactions.

Lastly, it is helpful to assess the steric effect of introduction of a $\lambda^6$-tetrafluorosulfanyl group. The steric demand of the group is consistent with the steric constraints of known liquid crystalline materials. The distance between C1 of the aromatic ring and acetylenic carbon of example 6a is 3.55 Å similar to the 4.01 Å distance associated with diphenylacetylene found in common structure element of liquid crystals and polymers, thus further suggesting the compound's utility for related applications. [Kirsch, P.; Bremer, M.; Kirsch, A.; Osterodt, J. Bis(4-nitrophenyl)tetrafluorosulfuranes: synthesis, isomerization and structural characterization. *J. Am. Chem. Soc.* 1999, 121, 11277-11280.]

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

All publications cited in this specification are herein incorporated by reference as if each individual publication were specifically and individually indicated to be incorporated by reference herein as though fully set forth.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

REFERENCES

Umemoto, WO 2008/118787 (Oct. 2, 2008).
Umemoto, U.S. Pat. No. 7,592,491 (Sep. 22, 2009).
Umemoto, U.S. Pat. No. 7,820,864 (Oct. 26, 2010).
Umemoto, U.S. Pat. No. 7,851,646 (Dec. 14, 2010).
Kirsch et al., DE 100 08 505 A1 (Dec. 12, 2000).
Kirsch, P.; Binder, W.; Hahn, A.; Jahrling, K.; Lenges, M.; Lietzau, L.; Maillard, D.; Meyer, V.; Poetsch, E.; Ruhl, A.; Unger, G.; Frolich, R. Super-fluorinated liquid crystals: towards the limits of polarity. *Eur. J. Org. Chem.* 2008, 3479-3487.

Kirsch, P.; Hahn, A. Liquid crystals based on hypervalent sulfur fluorides: Exploring the steric effects of ortho-fluorine substituents. *Eur. J. Org. Chem.* 2005, 3095-3100.

Matsushita, T.; Koseki, S. Theoretical Study on Mesogenic Core Structures of Nematic Liquid Crystalline Compounds. *J. Phys. Chem. B* 2005, 109, 13493-13498.

Kirsch, P.; Bremer, M.; Kirsch, A.; Osterodt, J. Bis(4-nitrophenyl)tetrafluorosulfuranes: synthesis, isomerization and structural characterization. *J. Am. Chem. Soc.* 1999, 121, 11277-11280.

Kirsch, Peer, et al. "Nematic Liquid Crystals for Active Matrix Displays: Molecular Design and Synthesis"; *Angewandte Chemie International Edition;* 2000; Pages 4216-4235; Volume 39; WILEY-VCH Verlag GmbH, Weinheim.

Kirsch, Peer, et al. "Liquid Crystals Based on Hypervalent Sulfur Fluorides: The trans-(Trifluoromethyl)tetrafluorosulfuranyl Group"; *European Journal of Organic Chemistry;* 2006; Pages 1125-1131; WILEY-VCH Verlag GmbH & Co. KGaA, Weinheim.

Umemoto, Teruo, et al. "Discovery of practical production processes for arylsulfur pentafluorides and their higher homologues, bis- and tris(sulfur pentafluorides): Beginning of a new era of "super-trifluoromethyl" arene chemistry and its industry"; *Beilstein Journal of Organic Chemistry;* 2012, Pages 461-471; Volume 8.

Darragh, John I., et al. "trans-Chlorotetrafluoro(trifluoromethyl)sulphur and its Reactions with Olefins and Acetylenes"; *Journal of the Chemical Society, Dalton Transactions;* 1973; Pages 2289-2293.

Abe, Takashi, et al. "CIS and TRANS ISOMERS OF BIS (PERFLUOROALKYL)SULFUR TETRAFLUORIDES"; *Inorganic and Nuclear Chemistry Letters;* 1973; Pages 465-468; Volume 9, Number 4; Pergamon Press; Great Britain.

Gupta, Krishna D., et al. "Syntheses of CF3SF4-Substituted Compounds"; *Inorganic Chemistry;* 1985; Pages 1457-1460; Volume 24; Number 10; American Chemical Society.

Denney, Donald B., et al. "Dialkyl- and Diaryltetrafluoropersulfuranes"; *Journal of the American Chemical Society;* Nov. 28, 1973; Pages 8191-8192; Volume 95; Issue 24.

Kitazume, Tomoya, et al. "Some Chemistry of Fluorinated Octahedral Sulfur Compounds; *Journal of the American Chemical Society;* Jan. 18, 1978; Pages 492-496; Volume 100; Issue 2.

Ou, Xiaobo, et al. "Oxidative fluorination of S, Se and Te compounds"; *Journal of Fluorine Chemistry;* 2000; Pages 279-283; Volume 101; Elsevier Science S.A.

Kirsch, Peer, et al. "Liquid crystals based on hypervalent sulfur fluorides Part 4. [1] Pentafluorosulfanyl alkanes and olefins"; 2006; Pages 610-619; Volume 127; Elsevier B.V.

The invention claimed is:

1. A compound of the Formula (I):

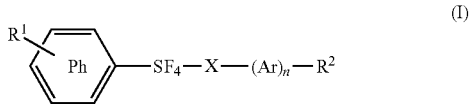

wherein

X and X' are independently selected from

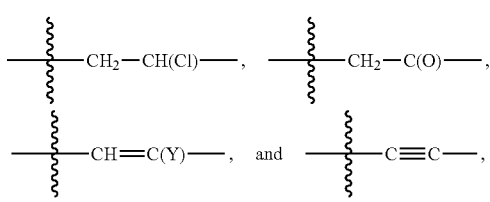

wherein

represents the point of connection to $SF_4$ residue;

Y is selected from hydrogen and chlorine;

Ar and Ar' are independently selected from aryl and heteroaryl, each optionally substituted by one or more substituents in addition to $R^2$ or $R^{2'}$ independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$;

n and n' are independently 0 or 1;

Ph ring is a phenyl ring optionally substituted by up to four substituents in addition to $R^1$, independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$;

$R^1$, $R^2$, and $R^{2'}$ are independently absent or selected from hydrogen, halogen, hydroxy, trifluoromethyl, pentafluorosulfanyl, cyano, nitro, carboxy, amino, mono- or di-$C_{1-4}$ hydrocarbylamino, carbocyclic and heterocyclic groups having from 3 to 12 ring members; and a group A-B wherein A is a bond, O, CO, $Z^1C(Z^2)$, $C(Z^2)Z^1$, $Z^1C(Z^2)Z^1$, S, SO, $SO_2$, $NR^c$, $SO_2NR^c$ or $NR^cSO_2$, and B is selected from hydrogen, carbocyclic and heterocyclic groups having from 3 to 12 ring members, and a $C_{1-8}$ hydrocarbyl group optionally substituted by one or more substituents selected from hydroxy, oxo, halogen, cyano, nitro, carboxy, amino, mono- or di-$C_{1-4}$ hydrocarbylamino, and carbocyclic and heterocyclic groups having from 3 to 12 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy, and wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$; and $R^1$ may additionally be —$SF_4$—X'—$(Ar')_{n'}$—$R^{2'}$; with the provisos that (a) when X is

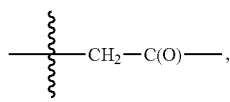

n is 0 and $R^2$ is A-B, where A is O; and (b) when X' is

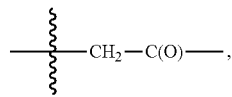

n' is 0 and $R^{2'}$ is A-B, where A is O;

$R^c$ is selected from hydrogen and $C_{1-4}$ hydrocarbyl; and $Z^1$ and $Z^2$ are independently selected from O, S, and $NR^c$.

2. A compound according to claim 1 wherein $R^1$, $R^2$, and $R^{2'}$ are independently absent or selected from hydrogen, fluorine, chlorine, bromine, trifluoromethyl, pentafluorosulfanyl, cyano, nitro, carboxy, amino, mono- or di-$C_{1-4}$ hydrocarbylamino; and a group A-B wherein A is a bond, O, CO, C(=O)O, OC(=O), OC(=O)O, or $NR^c$; and $R^1$ may additionally be —$SF_4$—X'—$(Ar')_{n'}$—$R^{2'}$.

3. A compound according to claim 2 wherein B is hydrogen or a $C_{1-8}$ hydrocarbyl group optionally substituted by one or more substituents selected from hydroxy, oxo, halogen, cyano, nitro, carboxy, amino, and carbocyclic and heterocyclic groups having from 3 to 6 ring members optionally substituted by one or more substituents selected from halogen, $C_{1-6}$ hydrocarbyl, $C_{1-6}$ hydrocarbyloxy, $C_{1-6}$ acyloxy, trifluoromethyl, trifluoromethoxy, and difluoromethoxy; and wherein one or more carbon atoms of the $C_{1-8}$ hydrocarbyl group may optionally be replaced by O, CO, S, SO, $SO_2$, $NR^c$, OC(=O), C(=O)O or OC(=O)O.

4. A compound according to claim 1 wherein $R^1$, $R^2$, and $R^{2'}$ are independently absent or selected from hydrogen, fluorine, chlorine, bromine, trifluoromethyl, cyano, nitro, carboxy, amino; and a group A-B wherein A is a bond, O, CO, C(=O)O, OC(=O), OC(=O)O, or $NR^c$ and B is hydrogen, a carbocyclic or heterocyclic group having from 3 to 6 ring members, or a $C_{1-8}$ hydrocarbyl group optionally substituted by one or more substituents selected from hydroxy, oxo, halogen, cyano, nitro, amino, or mono- or di-$C_{1-4}$ hydrocarbylamino, and wherein one or more carbon atoms of the $C_{1-8}$ hydrocarbyl group may optionally be replaced by O, CO, S, SO, $SO_2$, $NR^c$, OC(=O), C(=O)O or OC(=O)O; and $R^1$ may additionally be —$SF_4$—X'—$(Ar')_{n'}$—$R^{2'}$.

5. A compound according to claim 1 wherein n is 1.

6. A compound according to claim 5 wherein Ar is phenyl.

7. A compound according to claim 1 wherein n is 1, n' is 1, Ar is phenyl, and Ar' is phenyl.

8. A compound according to claim 1 of formula (IA) or (IB):

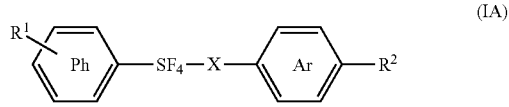

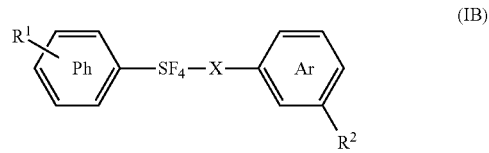

wherein Ar is optionally substituted by up to three substituents in addition to $R^2$, independently selected from halogen, nitro, trifluoromethyl, and $C_{1-4}$ hydrocarbyl.

9. A compound according to claim 1 wherein n is 0.

10. A compound according to claim 1 wherein $R^1$ and $R^2$ are independently selected from hydrogen, halogen, nitro, and an unsubstituted $C_{1-8}$ hydrocarbyl group, wherein one or more carbon atoms of the $C_{1-8}$ hydrocarbyl group may optionally be replaced by O, CO, S, SO, $SO_2$, $NR^c$, $Z^1C(Z^2)$, $C(Z^2)Z^1$ or $Z^1C(Z^2)Z^1$.

11. A compound according to claim 1 wherein the Ph ring is a phenyl ring substituted only by $R^1$.

12. A compound according to claim 1 wherein the Ph ring is a phenyl ring substituted by $R^1$ and one or more additional substituents independently selected from halogen, nitro, —SH, trifluoromethyl, and $C_{1-4}$ hydrocarbyl, wherein one or more carbon atoms of the $C_{1-4}$ hydrocarbyl group may optionally be replaced by O, CO, or $SO_2$.

13. A compound according to claim 12 wherein $R^1$ is not $—SF_4—X'—(Ar')_{n'}—R^{2'}$.

14. A compound according to claim 1 wherein $R^1$ is attached para to the $SF_4$ residue on Ph.

15. A compound according to claim 1 wherein one of $R^1$ and $R^2$ is $Z^a$, and the other is $Z^b$, and wherein $Z^a$ is selected from nitro, cyano, carboxy, and trifluoromethyl; and $Z^b$ is selected from hydroxy, $C_{1-8}$ hydrocarbyloxy, and mono- or di-$C_{1-4}$ hydrocarbylamino.

16. A compound according to claim 1 of the Formula (I-i), (I-ii), (I-iii), or (I-iv):

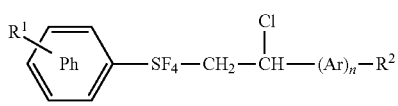
(I-i)

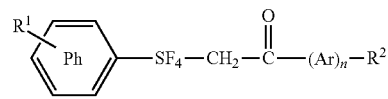
(I-ii)

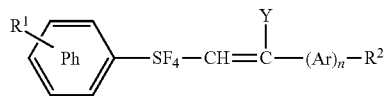
(I-iii)

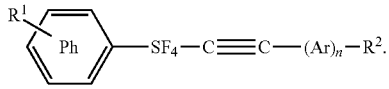
(I-iv)

wherein $R^1$, $R^2$, and $R^{2'}$ are independently selected from hydrogen, halogen, nitro, and a group A-B; and wherein $R^1$ may additionally be $—SF_4—X'—(Ar')_{n'}—R^{2'}$.

17. A liquid crystal display (LCD) comprising a compound according to claim 1.

18. A process for the preparation of a compound as defined in claim 1, which process comprises:

the reaction of a compound of the formula:

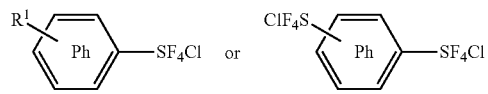

with an alkene or alkyne compound of the formula:

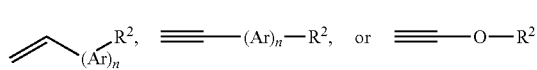

wherein the reaction is carried out in the presence of a free radical initiator, and wherein Ph, Ar, n, $R^1$, and $R^2$ are as defined in claim 1, and optionally thereafter converting one compound of the Formula (I) into another compound of the Formula (I).

19. A process according to claim 18 wherein the free radical initiator is a trialkyl borane.

20. A process according to claim 18 wherein the reaction is carried out in the presence of a saturated hydrocarbon solvent.

* * * * *